(12) United States Patent
Stivoric et al.

(10) Patent No.: US 7,153,262 B2
(45) Date of Patent: *Dec. 26, 2006

(54) WEARABLE HUMAN PHYSIOLOGICAL DATA SENSORS AND REPORTING SYSTEM THEREFOR

(75) Inventors: John Stivoric, Pittsburgh, PA (US); Francine Gemperle, Pittsburgh, PA (US); Christopher Kasabach, Pittsburgh, PA (US)

(73) Assignee: BodyMedia, Inc., Pittsburgh, PA (US)

( * ) Notice: Subject to any disclaimer, the term of this patent is extended or adjusted under 35 U.S.C. 154(b) by 272 days.

This patent is subject to a terminal disclaimer.

(21) Appl. No.: 10/313,255

(22) Filed: Dec. 6, 2002

(65) Prior Publication Data

US 2003/0065253 A1 Apr. 3, 2003

Related U.S. Application Data

(63) Continuation of application No. 09/419,600, filed on Oct. 18, 1999, now Pat. No. 6,527,711.

(51) Int. Cl.
*A61B 5/00* (2006.01)
(52) U.S. Cl. ............... 600/300; 128/905; 128/920; 600/301
(58) Field of Classification Search ........ 600/300–301, 600/306, 549, 557, 587, 595, 500, 503; 128/903–905, 128/920, 921, 923–925; 705/2–4; 482/4–9; 202/19; 374/100, 29–30; 455/73
See application file for complete search history.

(56) References Cited

U.S. PATENT DOCUMENTS

| | | |
|---|---|---|
| 4,129,125 A | 12/1978 | Lester et al. |
| 4,151,831 A | 5/1979 | Lester |
| 4,757,453 A | 7/1988 | Nasiff |
| 4,827,943 A | 5/1989 | Bornn et al. |
| 5,050,612 A | 9/1991 | Matsumura |
| 5,285,398 A | 2/1994 | Janik |
| 5,305,244 A | 4/1994 | Newman et al. |
| 5,353,793 A | 10/1994 | Bornn |
| 5,445,149 A | 8/1995 | Rotolo et al. |
| 5,491,651 A | 2/1996 | Janik |
| 5,555,490 A | 9/1996 | Carroll |
| 5,581,492 A | 12/1996 | Janik |
| 5,617,477 A | 4/1997 | Boyden |
| 5,719,743 A | 2/1998 | Jenkins et al. |
| 5,813,766 A | 9/1998 | Chen |
| 5,868,671 A | 2/1999 | Mahoney |
| 5,884,198 A | 3/1999 | Kese et al. |
| 5,908,396 A * | 6/1999 | Hayakawa et al. ......... 600/587 |

(Continued)

OTHER PUBLICATIONS

"Georgia Tech Researchers Develop First Smart T-shirt," Nov. 14, 1997, Georgia Institute of Technology press release.

*Primary Examiner*—Max F. Hindenburg
*Assistant Examiner*—Michael Astorino
(74) *Attorney, Agent, or Firm*—Metz Lewis LLC; Barry I. Friedman

(57) ABSTRACT

A sensor array and computing apparatus are located on the human body while maintaining said sensors and apparatus within a proximity zone of the body such that the mobility and flexibility of the body are not deleteriously affected by the presence of the apparatus. The system permits the dynamic monitoring of human physiological status data without substantial interference in human motion and flexibility. A processor is mounted within a pod location with or adjacent to a sensor pod location, or said processor may be electrically connected to said sensor.

8 Claims, 26 Drawing Sheets

U.S. PATENT DOCUMENTS 5,912,865 A  6/1999  Ortega
5,941,837 A * 8/1999  Amano et al. .............. 600/595
6,067,468 A  5/2000  Korenman et al.
6,247,647 B1  6/2001  Courtney et al.

* cited by examiner

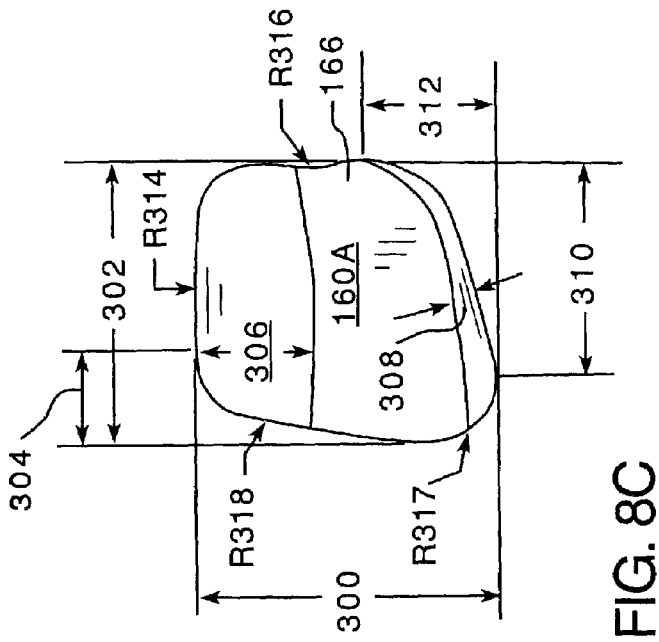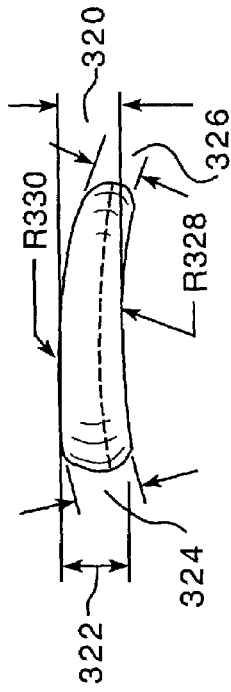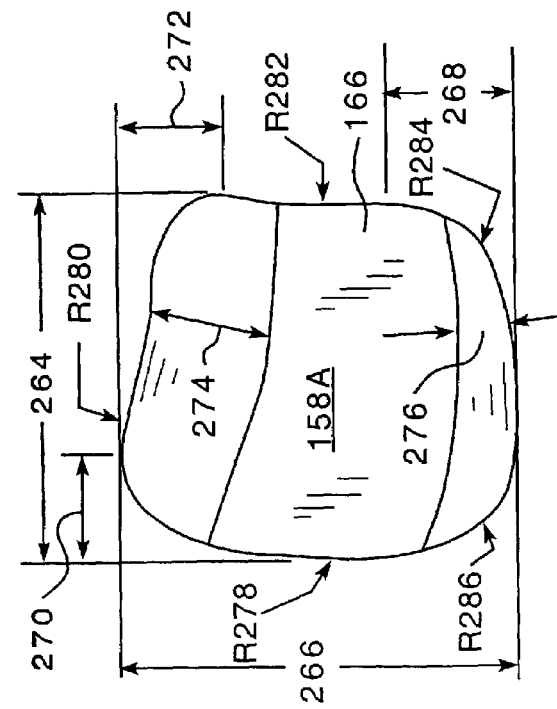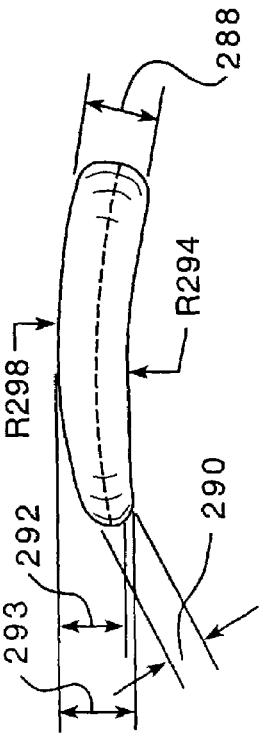
FIG. 8C
FIG. 8D
FIG. 8A
FIG. 8B

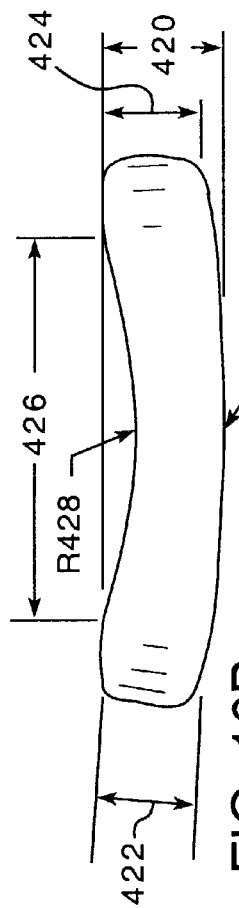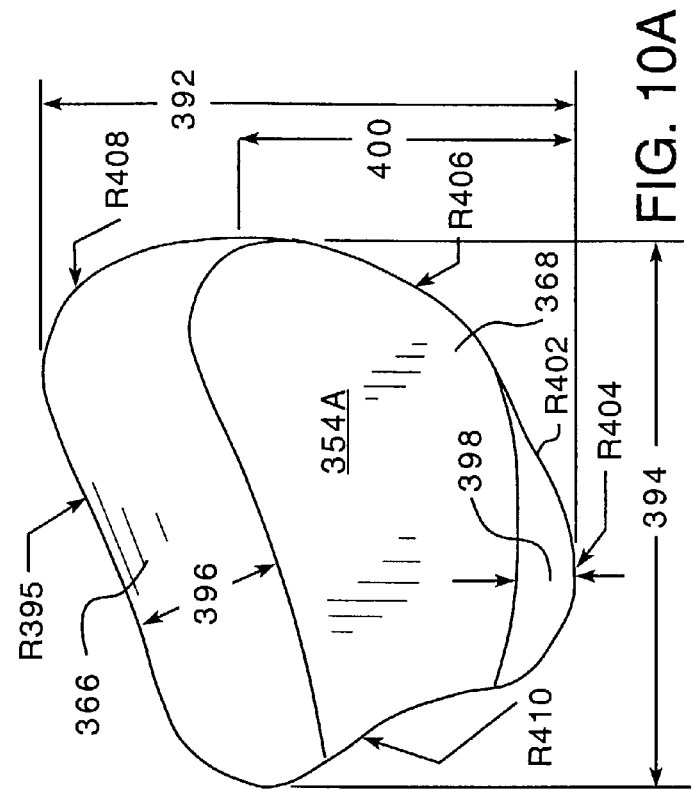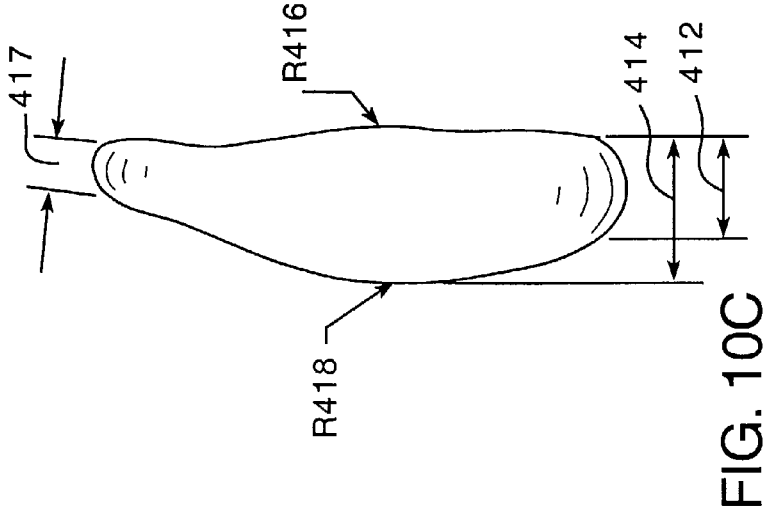

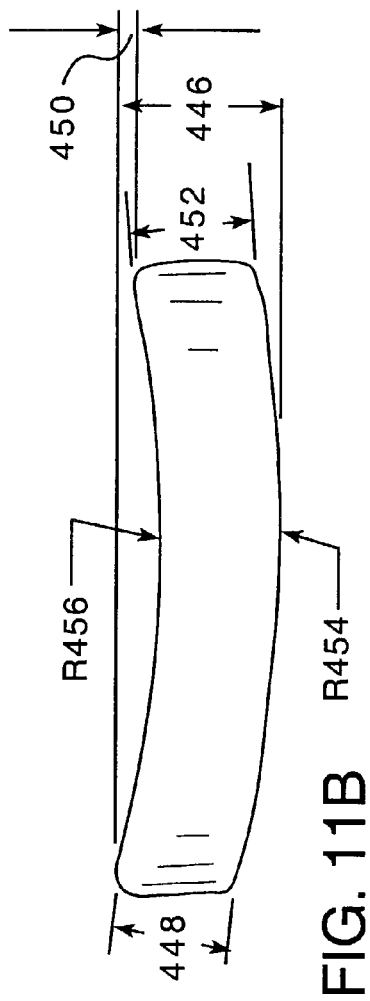
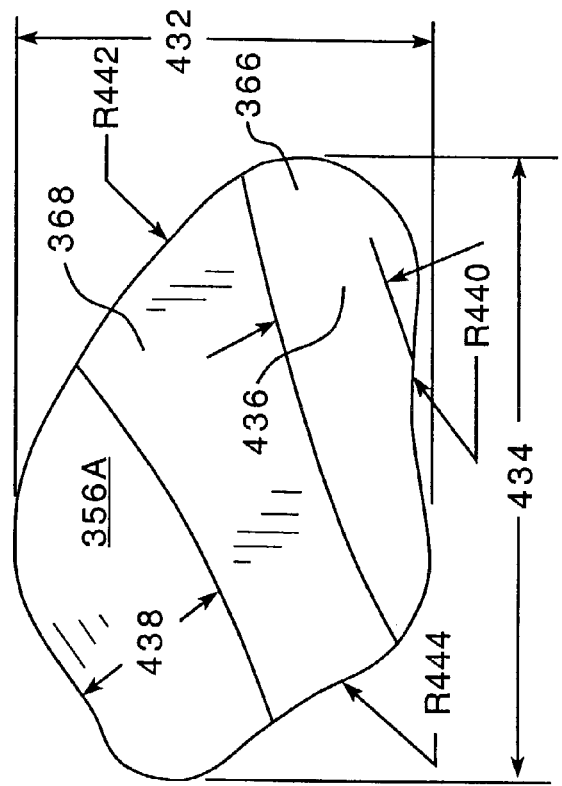
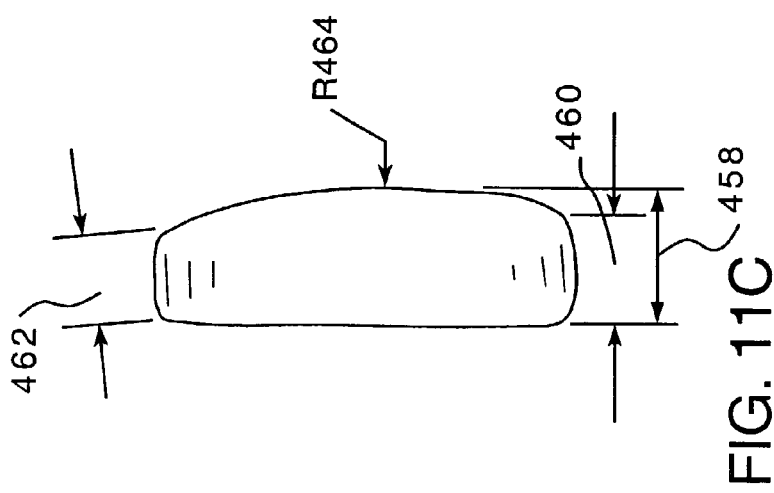
FIG. 11B
FIG. 11A
FIG. 11C

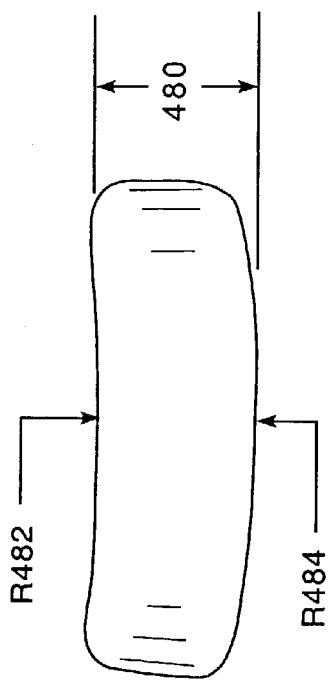
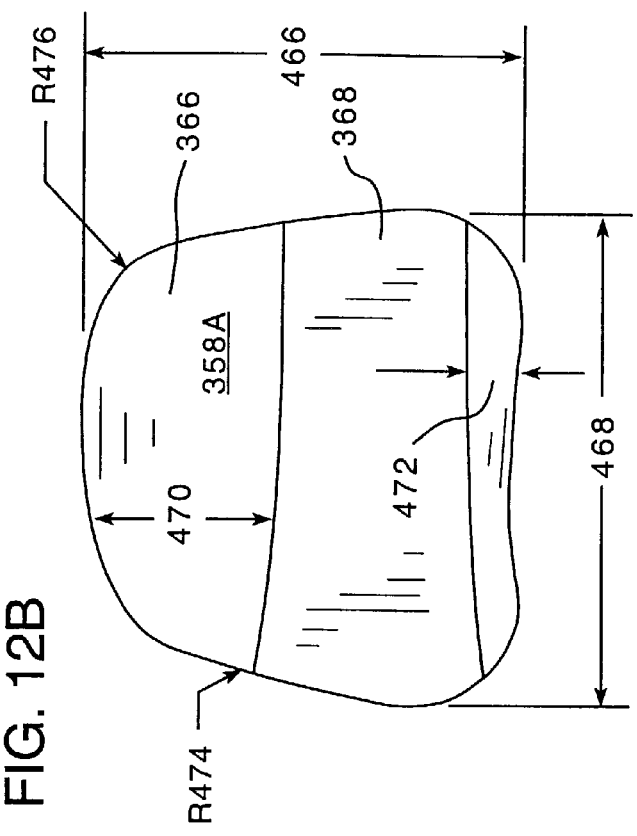
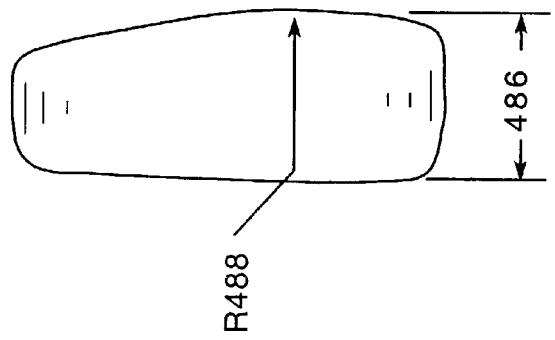
FIG. 12B
FIG. 12A
FIG. 12C

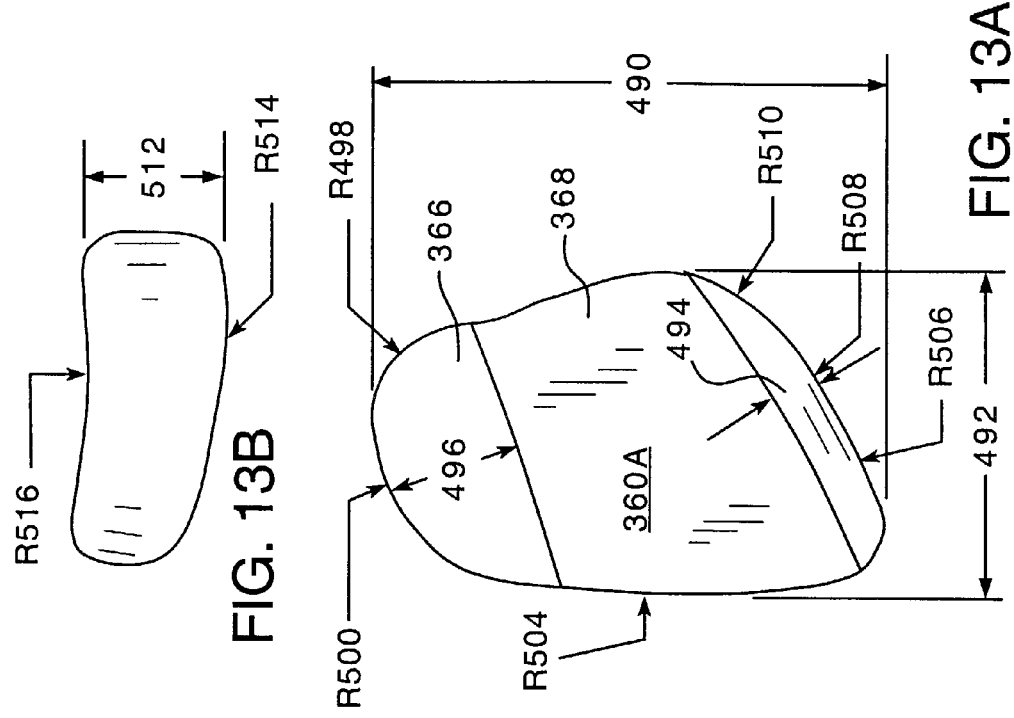
FIG. 13B
FIG. 13A
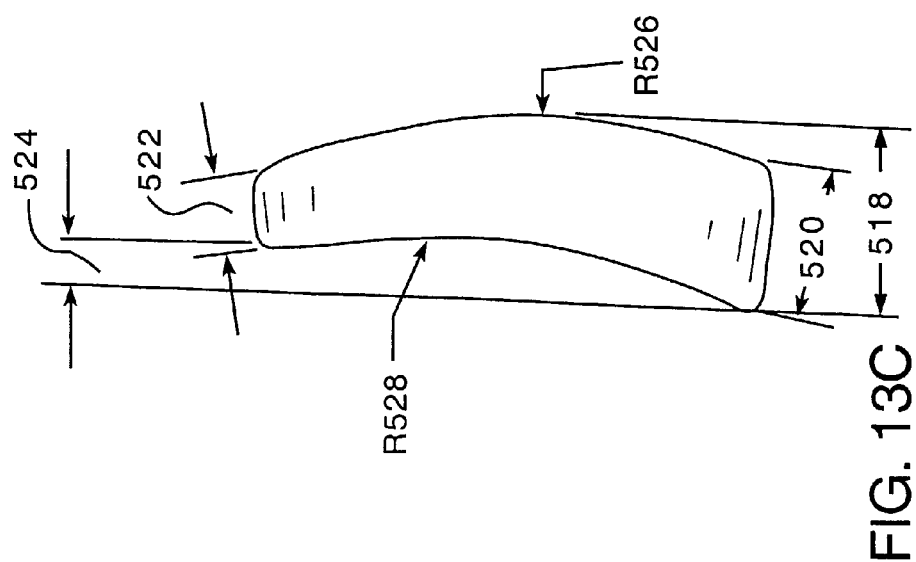
FIG. 13C

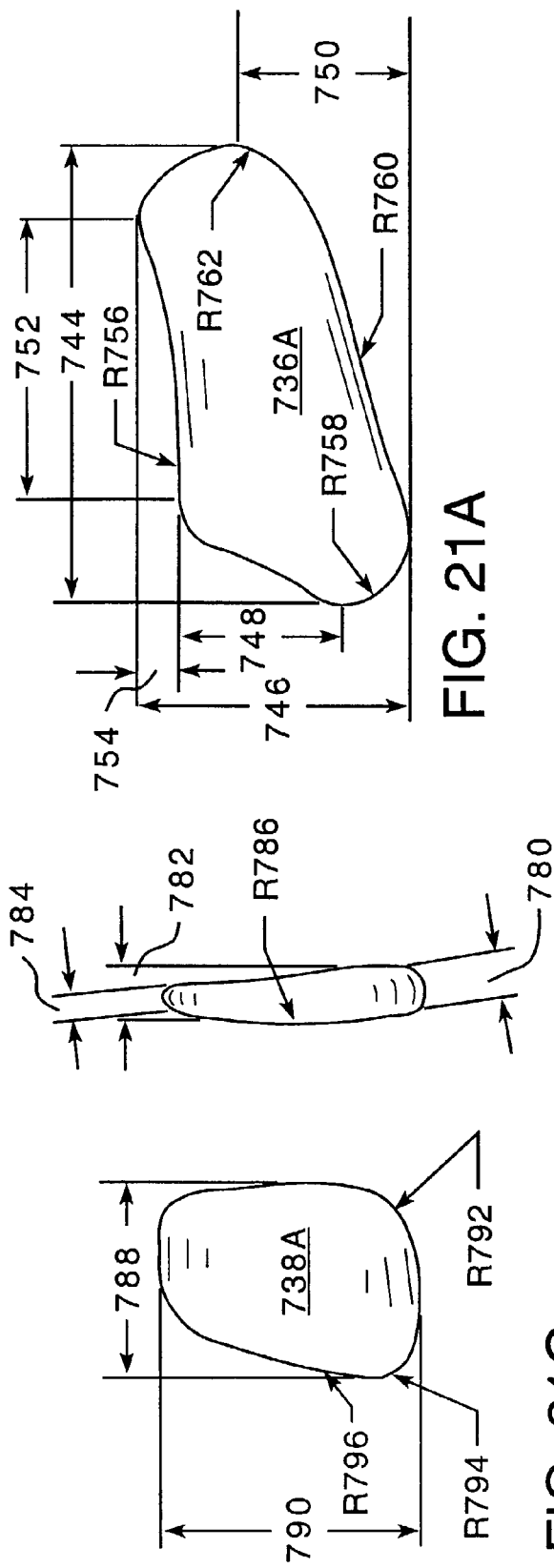
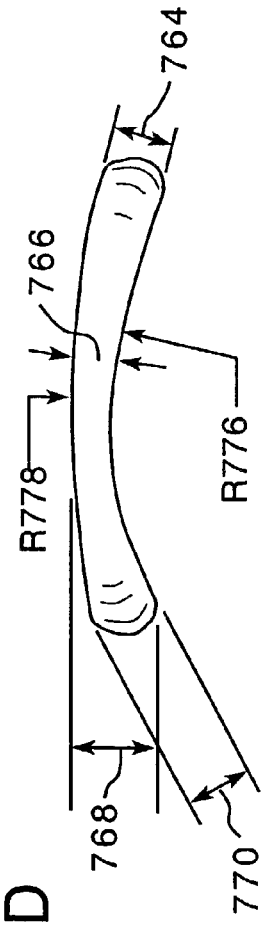
FIG. 21A
FIG. 21B
FIG. 21C
FIG. 21D

WEARABLE HUMAN PHYSIOLOGICAL DATA SENSORS AND REPORTING SYSTEM THEREFOR

The present application is a continuation of application Ser. No. 09/419,600, filed on Oct. 18, 1999 now U.S. Pat. No. 6,527,711.

BACKGROUND OF THE INVENTION

1. Field of the Invention

The present invention relates to computing hardware and sensor arrays which are suitable for affixation to the human body. More specifically, the invention relates to sensors and computing apparatus which are adapted to detect certain human physiological data and transmit such data and which are affixed to the human body in such a manner so as not to interfere with normal body flexibility or movement.

2. Description of the Prior Art

Monitoring of human physiological status data has received a high and growing level of interest in a number of medical, industrial, scientific and recreational disciplines. In certain circumstances where static data is sufficient for determining the status of a particular aspect of the human body, particularized monitoring sensors are applied to the appropriate portion of the body and data is collected for a short period of time. In these types of applications, the human subject may be in a static position, such as when blood pressure is measured, or actively engaged in movement, such as during a cardiac stress test. In either instance, a sensor is temporarily affixed to the body, either through a restraining device, friction or an adhesive material.

In the many applications, however, monitoring is limited to these short periods of time by limitations associated with the monitoring devices and the sensors themselves. Monitoring human physiological data on an extended, real-time basis presents many advantages to scientific researchers, medical professionals and individuals with a high level of interest in their own physiological condition.

A number of devices have been disclosed which attempt to enhance the portability and reduce the invasiveness of physiological sensors and the monitoring apparatus associated therewith. Furthermore, considerable development has been made in the reduction in size of computing devices and other electronic apparatus for use in close association with the human body.

Bornn, U.S. Pat. No. 5,353,793, issued Oct. 11, 1994, discloses a stretchable harness-like apparatus which enables physiological parameters of a patient to be measured while he or she is ambulatory or stationary. What is disclosed is a harness which encircles the torso and chest area of a patient. A series of circumferential straps are placed around the torso area with elongated shoulder supports supporting the circumferential bands from front to back over the shoulders. The harness-like apparatus includes certain sensors. The apparatus is specifically directed towards maintaining mobility and comfort while maintaining accuracy of measurement. A soft, resilient material is utilized to receive and restrain the encased sensors. A major shortcoming of dynamic body monitoring is identified in the reference which describes the utilization of resilient sensor supports under tension which creates monitoring artifacts caused by the relative movement of the sensors with respect to the patient's skin. The reference also identifies the utilization of electronic transmission means for communicating the collected data to external monitoring equipment. The Bornn device utilizes a uniform modulus of elasticity in the restraining bands which are selected of a material having such modulus of elasticity close to that of skin to maintain the sensors in a uniform position.

Janik, U.S. Pat. No. 5,285,398, issued Feb. 8, 1994, discloses a flexible, wearable computer, in the form of a belt, comprising a combination of microprocessor memory modules, power supply, signal relaying circuits, and a flexible, non-stretchable member with a protective covering device. In contrast to the Bornn reference, this device is intended to provide an entire wearable computer apparatus which is comfortable for the user to wear affixed to his or her body. The device incorporates a series of electrical apparatus divided into a plurality of small modules which are electrically connected along a non-resilient belt.

Kese, et al., U.S. Pat. No. 5,884,198, issued Mar. 16, 1999, discloses a portable radio which has its components distributed about a user's body, utilizing the body as a vehicle to carry the radio. This portable communication device was developed to overcome drawbacks associated with conventional portable radios through the distribution of the radio components and weight on a user's body in a more uniform manner.

Carroll, U.S. Pat. No. 5,555,490, issued Sep. 10, 1996, discloses a wearable support and interconnection structure for a modular micro computer system having a plurality of micro computer cards housed in a plurality of pockets linked by flexible circuitry and connectors within wearable garment. The reference discloses a vest-like apparatus having a series of electronic modules distributed thereacross. The garment is intended to be portable and lightweight while maintaining a level of functionality to allow the wearer to simultaneously operate the computer while engaged in a mobile activity.

Newman, et al., U.S. Pat. No. 5,305,244, issued Apr. 19, 1994, discloses a compact, self-contained portable computing apparatus which is completely supported by a user for hands-free retrieval and display of information for the user. The reference discloses a series of electronic components mounted upon a belt which is worn by the user together with a miniature video display device positioned proximate to the user's eye. A microphone is utilized to allow the user to execute commands without the utilization of his or her hands.

A significant shortcoming of the prior art devices, however, is that while they provide a lightweight and mobile computing or monitoring platform, they nevertheless severely restrict the flexibility and motion of the user. None of the prior art references disclose a specific location or series of locations proximate to the human body which would minimize or eliminate the interference of the body-mounted computer or sensor mechanism with normal or athletic bodily function and flexibility.

What is lacking in the art, therefore, is a sensor array and computing apparatus which is wearable on the human body in such a manner and placement that the user's motion and flexibility are not compromised.

SUMMARY OF THE INVENTION

An apparatus is disclosed which is adapted to specifically provide the ability to mount both sensors and computing apparatus on the human body while maintaining said sensors and apparatus within a proximity zone of the body such that the mobility and flexibility of the body are not deleteriously affected by the presence of the apparatus. The device is primarily comprised of a series of pods having rigid and flexible sections within which the sensors and computing apparatus may be housed. These pods are typically comprised of a rigid material having a minimum hardness or rigidity mounted in conjunction with certain more flexible sections to allow relative movement of the rigid material sections with respect to each other. The flexible material is further utilized to conform said rigid sections to certain pre-specified portions of the human body although it is to be specifically noted that under certain circumstances, the entire pod embodiment can be constructed of the flexible material. The pods are particularly sized and shaped to minimize interference with human motion and flexibility, and are mounted in certain distinct, pre-selected locations on the human body corresponding to the pre-specified shapes. It is to be specifically noted that each of the shapes disclosed herein comprises a maximum size and shape for each particular location. In any specific application, the minimization of the size and shape of any sensor or computing apparatus together with its rigid housing would be considered desirable to minimize interference with human flexion and motion.

The size, shape and location of each of the pod housings are specifically directed to not only certain locations of minimum interference when mounted upon the human body, but also for the specific intention of mounting sensors therein for the detection of certain human physiological status data. It is specifically contemplated that within at least one of the pod locations there will be mounted at least one specific sensor for contact with or proximate location near the human body for detection of physiological status data including but not limited to, temperature, galvanic skin response, pulse, blood pressure, respiration, activity, and certain electrical currents associated with electrocardiogram and electroencephalograph measurements.

The system is specifically intended to permit the mounting of one or more sensor devices, as well as electronic computing apparatus, to permit the dynamic monitoring of human physiological status data without substantial interference in human motion and flexibility. The systems are directed towards use in both medical care and scientific research. It is also contemplated that the system might be applied for the evaluation of human fitness, conditioning and the further development of ubiquitous, sympathetic and pervasive wearable computing apparatus. It is specifically intended that the sensors be placed within the specified locations defined by both a location determined by medical and scientific knowledge and the availability of a sensor pod defined according to the specification herein.

In a first embodiment of the system as a whole, one or more sensors are placed within the various pod locations as defined herein. A processor is mounted within the same pod location or an adjacent pod location, or said processor may be electrically connected to said sensor through a flexible material. Memory and storage means may also be provided as necessary to facilitate the processing function. Data from one or more sensors is acquired and processed according to pre-selected algorithms well known to those skilled in the art. It is specifically contemplated that this processing function may be performed by a processing means contained within the pods mounted upon the human body or by external monitoring hardware and software, as will be described herein. The first embodiment, as described, would process said data onboard the human body and transmit that data in a processed state to an external monitor through certain wire-based or wireless technologies as are well known to those skilled in the art. Such wireless technologies would include radio frequency, infrared transmission, audio and magnetic induction. It is specifically contemplated that said wireless technologies would include both open channel radio frequency transmission as well as transmissions which utilize telecommunications technologies, such as wireless telephoning and paging systems. In this first embodiment, there is optionally provided a graphical, visual, audible, tactile or haptic output means so that certain data might be displayed or otherwise communicated instantaneously to the wearer in the form of a numerical output or a series of indicator lights.

In a second embodiment, human physiological status data is merely compiled within the apparatus mounted upon the human body and is transmitted, in an unprocessed state, to an external monitoring means. In this embodiment, no onboard output or display means is contemplated.

It is further specifically contemplated that the system, as described herein, forms a subset of a larger human physiological status data recording and reporting system for which the material described herein forms the data acquisition and reporting segment.

The rigid and flexible pods described herein are defined by a proximate space adjacent the human body at certain predefined locations where interaction with human motion and flexibility are minimized. The wearability of the sensor and hardware apparatus is specifically defined as the interaction between the human body and the wearable objects. The wearable pods described herein comprise three-dimensional spaces on the body best suited for comfortable and unobtrusive wearability by design. The requirements of wearability further defines the use of the human body as a support environment for the various products and sensors that will be mounted thereupon. It is intended that these wearable forms be universally applicable to a high percentage of the wearing population. While it would be considered impossible to design a set of standard forms which would be applicable to 100% of the male and female population, given the wide disparity of the sample set, the specific design of the forms disclosed is intended to apply from the fifth to the ninety-fifth percentile of the population.

There are thirteen primary factors which define the design of the wearable products. These are:
1. Placement;
2. Definition of the shape of the object;
3. The dynamic structure of the object relating to human movement in proximity thereto;
4. Human perception of the space proximate to the body;
5. Sizing as applied to the target group of body sizes;
6. Attachment means to the body;
7. Containment of objects within the defined space;
8. Weight;
9. Accessibility to human interaction;
10. Sensory interaction with the body;
11. Thermal interaction with the body;
12. Aesthetics;
13. Long-term effects on usability and wearability.

The criteria used for determining the placement of the forms on the human body are:
1. Areas that have relatively small size variance across adults;
2. Areas that have low movement and flexibility, even when the body is in motion; and
3. Areas that maximize available surface area or minimize surface irregularities.

The general areas determined to be the most unobtrusive are the cranial area, collar area, the tricep area, the forearm area, the rib cage area, the waist and hip area, the thigh area, the shin area and the top of the foot area.

With respect to the form of the various proximity spaces in the containment pods placed therein, a core concept includes forming a concavity on the inside surface of the material to accept a generally convex exterior surface of the human body. Exterior surfaces of the pods are generally convex to deflect objects and avoid bumps and snags. Furthermore, tapering and radiusing of the sides, edges and corners creates safe, soft and stable forms. In certain circumstances, chamfering and scalloping of surfaces are utilized to minimize specific interaction with proximate body parts or physical objects and facilitate extended contact upon motion.

Human movement provides a significant constraint in terms of the placement and shaping of the forms defined herein. Defining the shapes with respect to these movements can be accomplished in one of two ways: (1) by designing around the more active areas of the joints, or (2) by creating spaces, such as the aforementioned chamfering or scalloping, into which certain body parts can move.

It is well known to those skilled in the art that the brain perceives an aura or proximate space around the body that should be considered the intimate space that is perceptually considered part of the body by the brain. This is generally considered to be between 0" and 5" from the majority of the body space. The particular challenge in defining the containment forms is the variability of size, weight, and muscle mass of human physique. Certain static anthropometric data is utilized to achieve near universal application of forms which are comprised of rigid and flexible sections. Flexible areas are generally utilized to join certain solid forms or extend exterior to the solid forms in wing-like protrusions. These wing-like protrusions may also incorporate a transition to attachment means for temporarily affixing the sensors and other apparatus to the body. It is specifically contemplated that in many applications, wrapping the form around the body, rather than using single point fastening systems such as clips or shoulder straps, is preferred. While not specifically disclosed, attachment systems are required for utility, which must accommodate various physical sizes and shapes designed for size variations. This is typically obtained in two ways: the first being adjustability, such as straps with buckles; the second is through the use of standardized sizing systems. The latter has been adopted in the preferred embodiment design to the extent that the rigid pods are generally standardized. In each embodiment, conventional resilient fabrics may be utilized to affix the pods to the body. Alternatively, and preferably, the pods may be incorporated into a garment.

These and other objectives, features and advantages of the present invention will be more readily understood upon consideration of the following detailed description of the preferred embodiments and the accompanying drawings.

BRIEF DESCRIPTION OF THE DRAWINGS

All drawings identified herein are labeled for directionality and physical reference as applied to the human body itself. E.g., references to "right" refer to the right-hand side of the wearer.

FIG. 8A is a plan view of a third pod of said rightmost half of a rib cage pod set. FIG. 8B is a side elevational view of the pod shown in FIG. 8A. FIG. 8C is a plan view of a fourth pod of the same pod set. FIG. 8D is a side elevational view of the pod shown in FIG. 8C.

FIG. 10A is a plan view of a first pod of a leftmost half of a torso-mounted pod set. FIG. 10B is a first side elevational view of the pod illustrated in FIG. 10A. FIG. 10C is a second side elevational view of the pod illustrated in FIG. 10A.

FIG. 11A is a plan view of a second pod of a leftmost half of a torso-mounted pod set. FIG. 11B is a first side elevational view of the pod illustrated in FIG. 11A. FIG. 11C is a second side elevational view of the pod illustrated in FIG. 11A.

FIG. 12A is a plan view of a third pod of a leftmost half of a torso-mounted pod set. FIG. 12B is a first side elevational view of the pod illustrated in FIG. 12A. FIG. 12C is a second side elevational view of the pod illustrated in FIG. 12A.

FIG. 13A is a plan view of a fourth pod of a leftmost half of a torso-mounted pod set. FIG. 13B is a first side elevational view of the pod illustrated in FIG. 13A. FIG. 13C is a second side elevational view of the pod illustrated in FIG. 13A.

FIG. 21A is a plan view of a first pod of the foot-mounted pod set illustrated in FIG. 20. FIG. 21B is a side elevational view of the pod illustrated in FIG. 21A. FIG. 21C is a plan view of a second pod of said foot-mounted embodiment illustrated in FIG. 20. FIG. 21D is a side elevational view of the pod illustrated in FIG. 21C.

DESCRIPTION OF THE PREFERRED EMBODIMENTS

Figure 1:
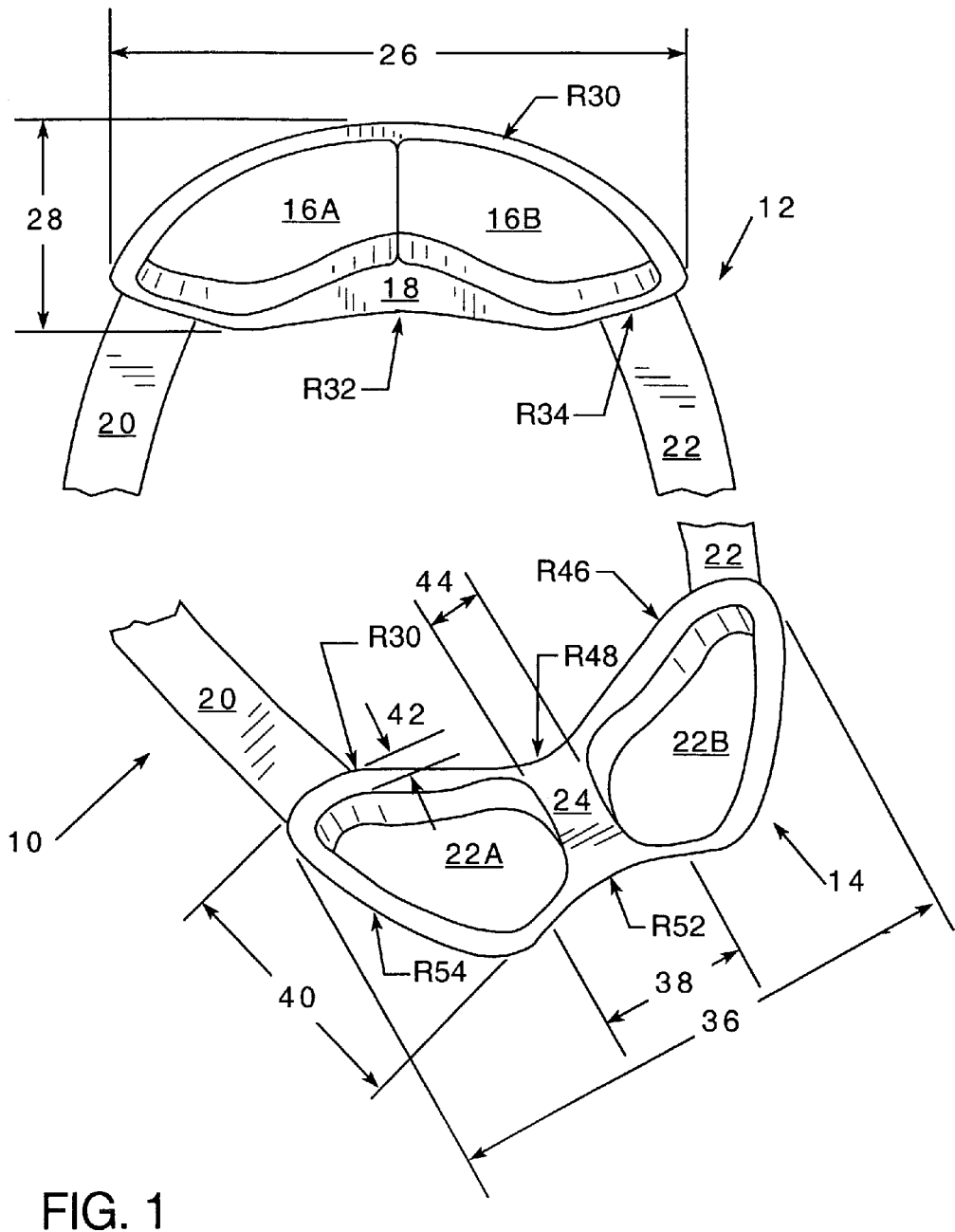
FIG. 1 is a plan view of a collar embodiment of a pod.

With respect to all of the Figures illustrating the pods and pod sets, all major dimensions and arcuate sections are defined in inches. Minor and transitional arc sections are considered to be within the ambit of knowledge and skill of those skilled in the art for constriction purposes. All the rigid form edges illustrated have radii of at least ⅛" and are variable up to ¾". Chamfers, scallops and bevels are at least 3° but are variable and can sweep to 50° in certain circumstances as described herein. Pods identified with the letter "A" are mirror equivalents of the unmarked reference numerals.

All rigid forms are of a minimum of 100D durometer of hardness and may be comprised of any material. In the event that the pods are intended for the support of sensor or related electronic material, it is preferable that the pods be comprised of an insulating material. Flexible sections are preferably comprised of 75–90D material, if one or either sides of the material are scored to facilitate bendability. If no surface treatment is used, the flexible materials are preferably comprised of 30–75D material. Flexible areas are preferably also stretchable, in the range of 14–16 ounces of tension for displacement of one-sixteenth inch to 3 inches.

Referring now to FIG. 1, the collar or neck embodiment of a pod set is illustrated. This set preferably comprises four pods, 16A, 16B, 22A and 22B, mounted within a flexible collar. The flexible collar may be of a unitary construction or comprised of front section 18, rear section 24, and connecting sections 20 and 22. Either or both connecting sections 20 or 22 may be of unitary construction and stretchable to the point that the head may be inserted therebetween or may be connected through a well known fastening means. The collar in embodiment 10 has a front section 12, which is primarily comprised of collar front flexible section 18 having a length 26 of 7.89 inches and a width 28 of 2.82 inches. The front edge of section 12 has a radius R30 of 4.42 and a rear radius R32 of 6.3. Rigid pods 16A and 16B are mounted thereon with a flexible space deposed therebetween. While pod 16A and 16B may abut each other, a space of at least ⅜ inch is preferably disposed therebetween. The flexible section is radiused at the point where the flexible restraints 20 and 22 are affixed having a radius R34 of 4.0. Flexible portion 18 of front section 12 is preferably ½ inch larger than the pods having a boundary of approximately ¼ inch around the perimeter thereof. Flexible members 20 and 22 preferably have a length of 6.4 inches and connect front section 12 to rear section 14. Rear section 14 is provided with a length 36 of 7.27 inches and a width 40 of 3.50 inches. Rear pods 22A and 22B are disposed thereon with a preferable border 42 of 0.29 inches and a distance therebetween 44 of 0.75 inches. Flexible section 24 is radiused at its rear surface R52 to a dimension of 2.24 inches and the frontmost facing edge R48 has a dimension of 0.94 inches. Left and right side perimeters of flexible section 24 have a radius R54 of 4.84. Radius R48 transitions to radius R46, moving outwardly, having a dimension of 4.42 and further transitions to a radius R50 of 1.50 inches where the leftmost and rightmost corners are encountered.

Figure 2A:
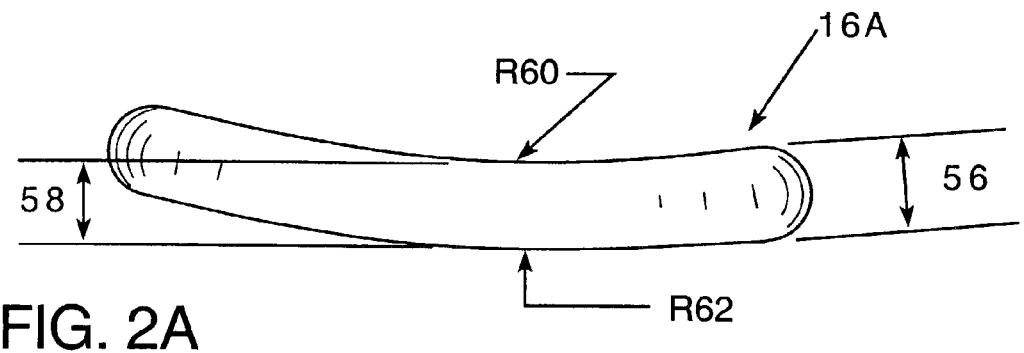
FIG. 2A is a side elevational view of a first pod as illustrated in FIG. 1.
Figure 2B:
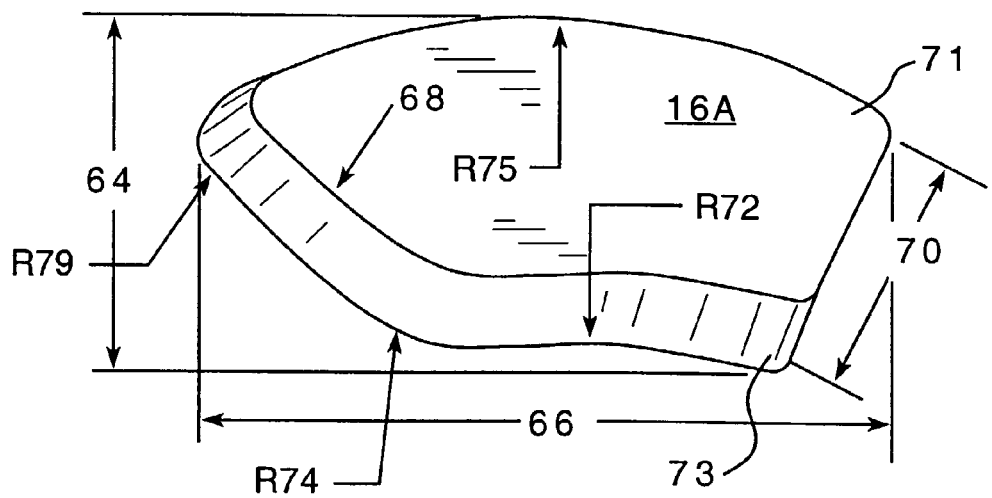
FIG. 2B is a plan view of the same pod.

Referring now to FIG. 2, pod 16A is illustrated in FIG. 2B having a length 66 of 4.03 inches and a depth 64 of 1.89 inches. Pod 16A, as well as 16B, for which all dimensions are identical but mirrored, has a chamfered edge 73 along the rearmost side, having a depth 68 of 0.4 inches. Pod 16A is provided with a lateral dimension 70 extending from front to rear along the rightmost edge of 1.34 inches as measured from the radius transitional point of the corners forming a roughly trapezoidal shape. Pod 16A is provided with a curved surface along the chamfer 73 beginning from the rear right corner, radius R72, having a dimension of 4.35 inches, radius R74, having a dimension of 1.5 inches, transitioning to corner radius R79, having a dimension of 0.25 inches. Referring now to FIG. 2A, pod 16A is seen in a side elevational view having a depth 58 of 0.45 inches and an inner radius R60 of 32.24 inches and an outer radius R62 of 9.62 inches. Pod 16A is slightly tapered from right to left, as seen in FIG. 2A, having a rightmost greater dimension 56 of 0.45 inches, tapering at the centermost point to thickness 58 of 0.43 inches.

Figure 3A:
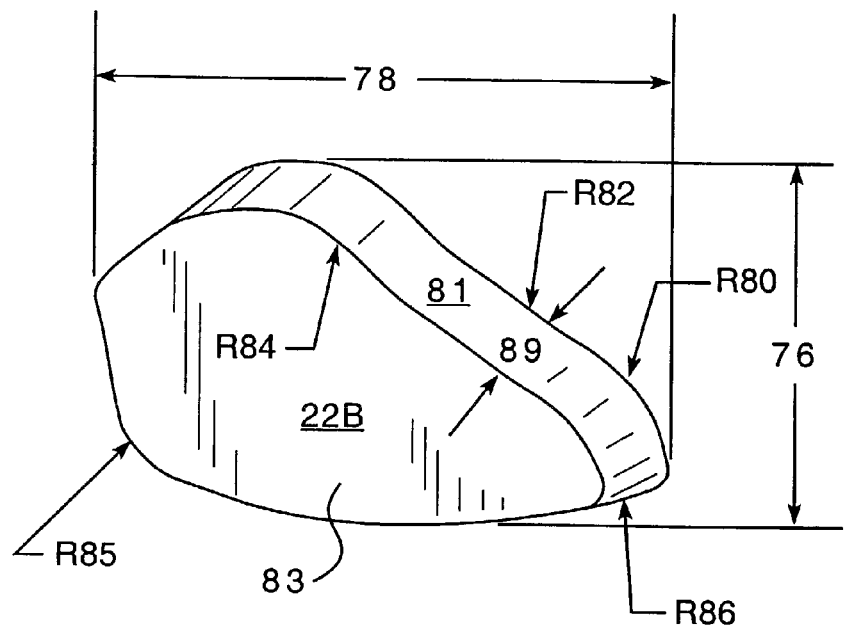
FIG. 3A is a plan view of a second pod as illustrated in FIG. 1.
Figure 3B:
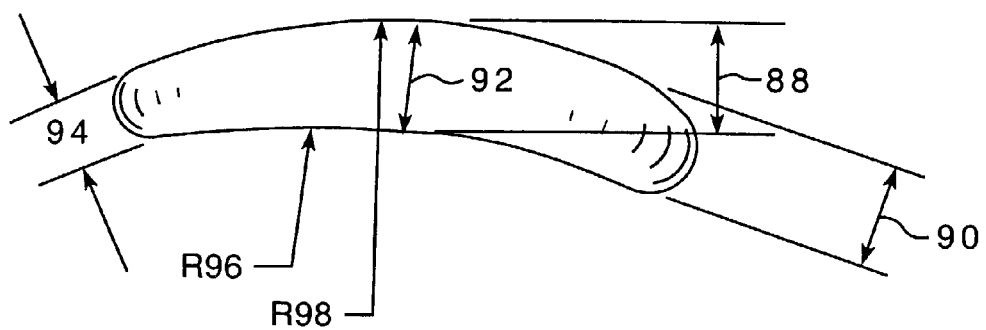
FIG. 3B is a side elevational view of the same pod.

Referring now to FIG. 3A, pod 22B is provided with a length 78 of 3.41 inches and a width 76 of 2.25 inches. It is to be specifically noted that pod 22A has the same dimensions as pod 22B in a mirrored embodiment. Pod 22B is provided with chamfer section 81 having a width 89 of 0.42 inches. The rearmost edge of pod 22B is provided with a curved radius R86 of 4.45 inches, transitioning in a leftmost direction to R85 of 0.75 inches along the front surface of the chamfered edge. Radius R80 is provided with a dimension of 0.9 inches which transitions to radius section R82 having a dimension of 4.69 inches. Referring now to FIG. 3B, pod 22B is provided with a tapered cross-sectional dimension having a thickness 90 of 0.58 inches tapering to a smaller dimensional thickness 94 of 0.43 inches. At the mid-point 92, a dimension of 0.67 is provided. Pod 22B is provided with a outer radius surface R98 of 3.58 inches and an inner radius surface R96 of 6 inches. As applied to the body, front section 12 is located at the top of the pectoral muscle, just below the clavicle, and is centered on the sternum of the user. Straps 20 and 22 flow between the meeting point of the shoulder and neck. Rear section 14 is placed on top of the upper portion of the trapezius muscle above the spine of scapula, but in no application should be placed lower than the last cervical vertebra C7 and no higher than the fifth cervical vertebra C5. Furthermore, in no circumstances is width 36 to exceed the size of the spine of scapula bone and the upper trapezius muscle. Front section 12, and more specifically, radius R30, are intended to be defined by the first and second ribs below the collar bone. Pods 16A and 16B rest on the pectoral muscle close to the body's center of gravity and out of the way of arm movement. With respect to rear section 14, the pods are designed to allow full movement of the neck and shoulders while utilizing the load bearing space near the sensory organs of the head. The pods are designed to move and float over flexed trapezius muscles with radii R48, R46 and R50 determined by the movement of the neck, and the radius R52 determined by the movement of the shoulder blades and the spine.

It is to be specifically noted that the pods of any of the embodiments described herein as discreet constructions may be joined by flexible material in a variety of combinations and subcombinations. For example, the collar, tricep and rib cage embodiments might be joined into a unitary, flexible garment, such as a shirt, having the appropriate resiliency and modulus of elasticity as described herein.

Figure 4:
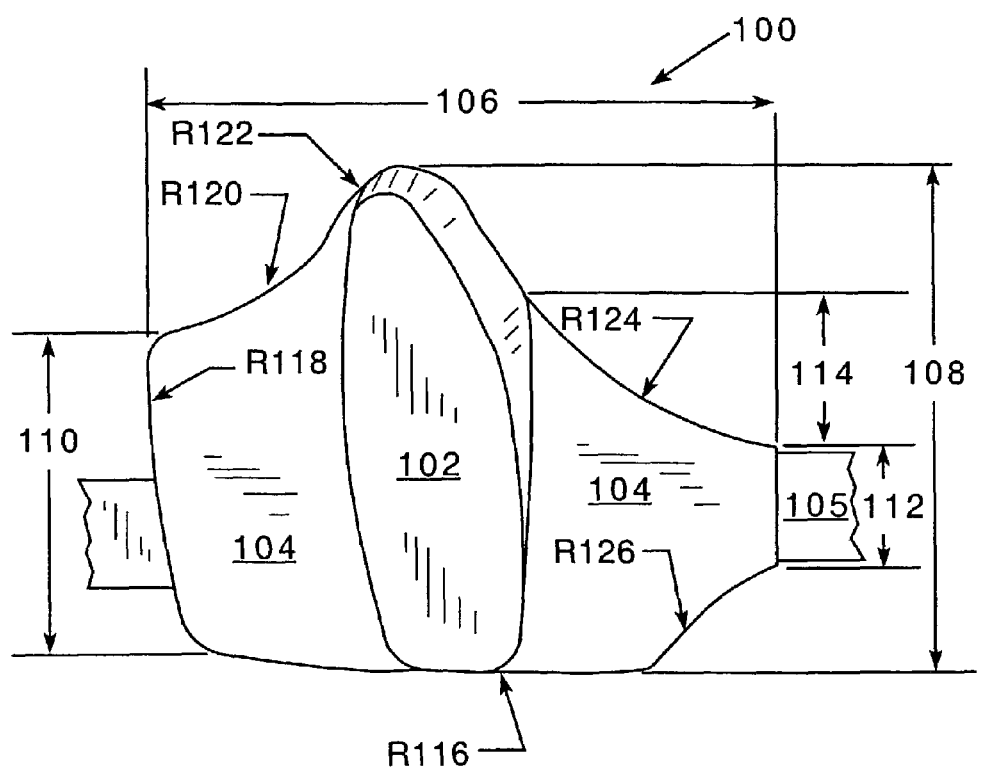
FIG. 4 is a plan view of a tricep embodiment.
Figure 5A:
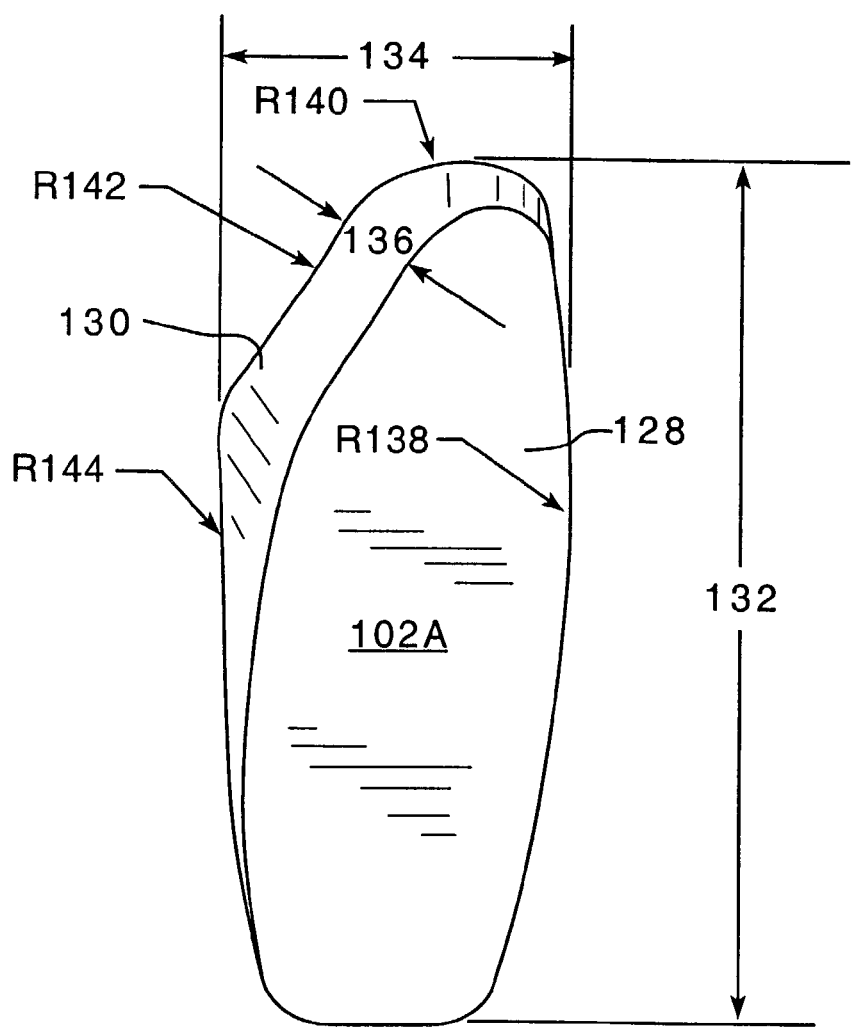
FIG. 5A is a plan view of the pod section illustrated in FIG. 4.

Referring now to FIG. 4, tricep embodiment 100 is adapted for affixation to the upper arm and is centered on the tricep, including all three areas of that muscle, the long head, the lateral head and the tendon. It is intended to be mounted at least one inch above the elbow joint and at least one-half inch below the deltoid muscle. Referring briefly to FIG. 5, width 134 of pods 102 and 102A, should not exceed the width of the entire tricep muscle of the user. The form of this embodiment is designed to allow movement of the flesh associated with both the shoulder and elbow joints, and includes flex zones in flexible portion 104 which taper inward as they wrap around the biceps. Rigid pod section 102 is affixed within flexible section 104. Flexible section 104 is intended to reach around the biceps, and the ends thereof may abut each other in certain applications where the user has a small arm circumference, but in no event should the ends of flexible section 104 overlap. The topmost curvature of the flexible section 104 is intended to follow the bottom edge of the deltoid muscle while the bottom curve of the same flexible section is intended to mimic the curvature of the lower portion of the bicep. Contact with the humerus bone is to be specifically avoided in order to avoid interference with sensitive tendons and nerves at this juncture. The tricep embodiment 100 is provided with a overall height 108 of 5.12 inches and an overall width 106 of 6.48 inches. The front edge of this embodiment, flexible section 104, has a height 110 of 3.22 inches, as measured from the completion of the corner radii at the point of transition to the rearward edges. This edge is provided with a radius R118 of 10 inches. The topmost edge, moving from front to rear of the flexible section, is provided with a concave radius R120 of 2 inches, transitioning to a convex radius R122 of 0.84 inches to support the rigid pod. Rearward of the pod is a convex radius R124 of 4.58 inches which section has a height 114 of 1.55 inches. The rearwardmost edge 112 has a dimension of 1.28 inches, as measured inclusive of the corner radii. The rearwardmost edge 112 is transitioned into the bottommost edge with a concave radius R126 of 2.61. Lastly, a concave lower section R116 is provided with a radius dimension of 15 inches.

Figure 5B:
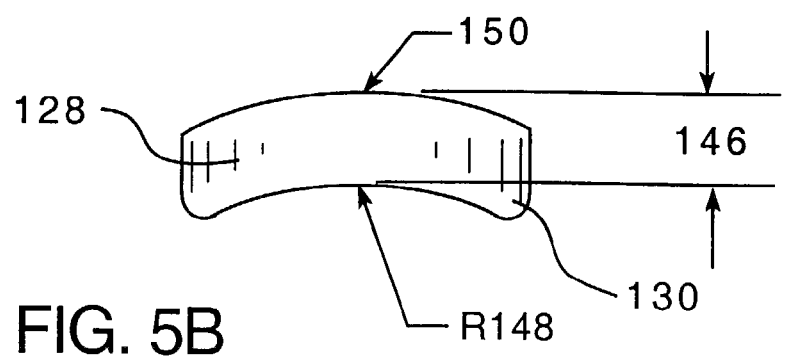
FIG. 5B is a side elevational view of the same pod.

Referring now to FIG. 5, the pods 102 and 102A of the tricep embodiment are provided with an overall height 132 of 5.05 inches and an overall width 134 of 1.99 inches. Pods 102 and 102A are provided with a chamfered area having an overall width 136 of 0.45 inches which is tapered at each end in a smooth transition. The topmost edge of pod 102A is provided with a convex radius R140 of 0.81 inches which transitions rearwardly to a concave radius R142 of 4.58 inches and transitions again to a convex rearward facing edge R144 having a radius of 9.95 inches. The front edge of pod 102A is provided with a radius R138 of 10 inches. Referring to FIG. 5B, the pod is provided with an overall convex section having a mid-point thickness 146 of 0.5 inches, an outer radius face R150 of 8.62 inches, and an inner radius face R148 of 1.91 inches.

Figure 6:
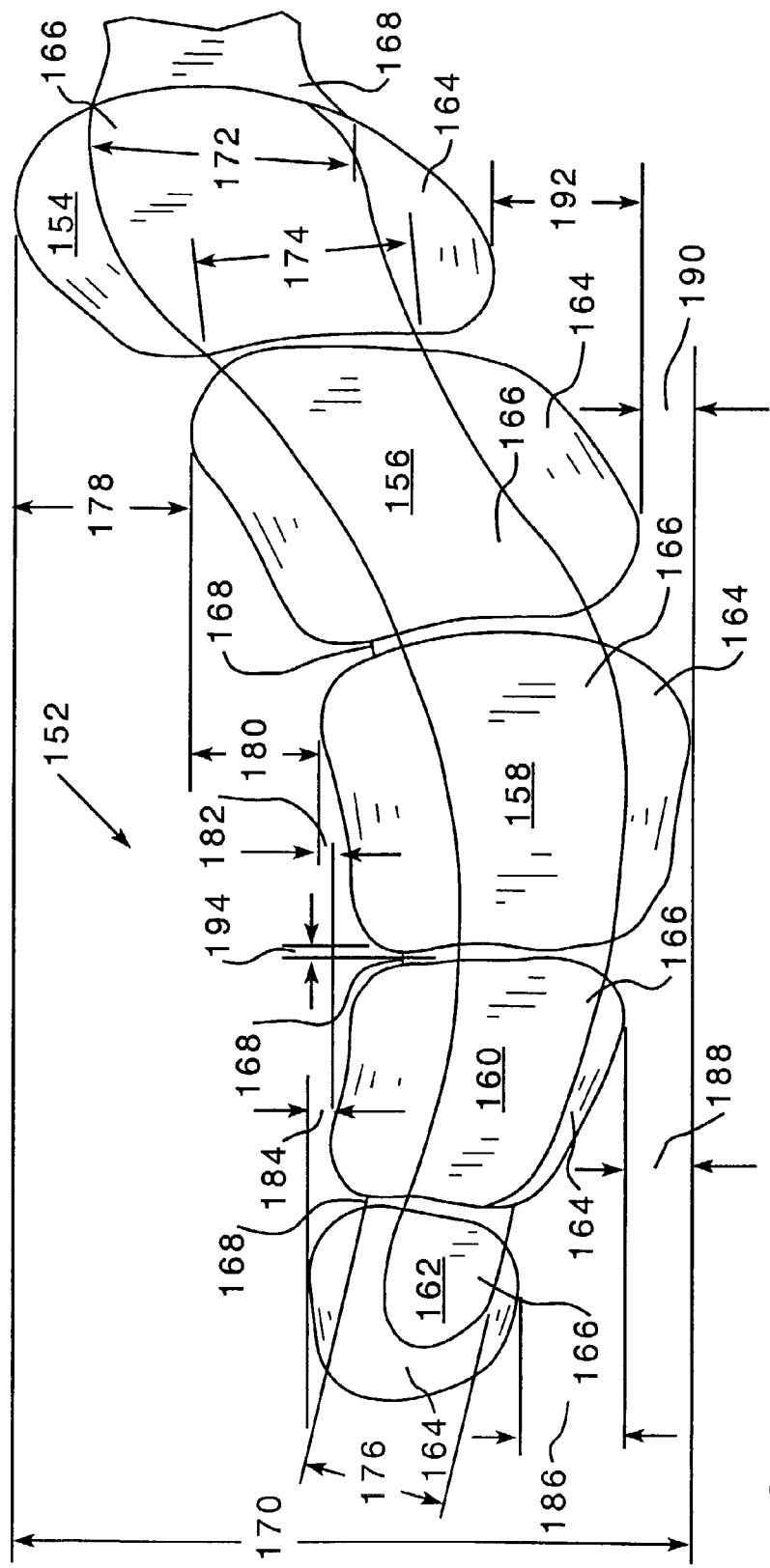
FIG. 6 is a plan view of the leftmost half of a rib cage embodiment of a pod set.

Referring now to FIG. 6, the upper torso embodiment is shown. It is to be specifically noted that the leftmost half of the upper torso portion is illustrated. The rightmost half being an identical mirror image thereof. Upper torso section 152 has an overall length of 27.72 inches in its complete form, and an overall height 170 of 6.91 inches. It is primarily comprised of five pods, 154, 156, 158, 160 and 162, being disposed along a flexible member 168. Each of the pods is provided with an overall convex surface 164 having a chamfered section 166 extending therealong, as will be described in more detail. It is to be specifically noted that chamfered section 166 is intended to extend smoothly across the length of all five pod sections. Upper torso embodiment 152 has a distance of approximately 1 inch between the first pod of the right and leftmost sections. First upper torso pod 154 has a major chamfer width 172 of 2.75 inches, tapering to a width 174 at the leftmost edge thereof, which coincides with the width of the flexible member 168 thereunder. Flexible member 168 continues its gradual taper to a leftmost dimension 176 of 1.49 inches at the leftmost edge of upper torso embodiment 152. Each of the pods is disposed a distance 194 of approximately 0.13 inches therebetween. Second upper torso pod 156 is mounted a distance 178 of 1.85 inches from the topmost point of pod 154 to the topmost point of second pod 156. A bottom distance 192 of 1.50 inches is provided between the lowermost point of first pod 154 and the lowermost point of second pod 156. Third pod 158 is mounted a distance 180 of 1.35 inches between the topmost points of second pod 156 and third pod 158 at a distance 190 of 0.52 inches between the lowermost points of second pod 156 and third pod 158. Third pod 158 represents the lowest point in the curvature of the five pods from first pod 154 through fifth pod 162. Fourth pod 160 is provided a distance 188 of 0.5 inches between the lowermost point of fourth pod 160 in the lowermost point of third pod 158. Fifth pod 162 is provided a distance 184 of 0.19 inches between the uppermost point of fifth pod 162 and the uppermost point of fourth pod 160, and a distance 186 of 1.04 between the lowermost points of those same two pods. Pods 154 through 162 follow the general curve that sweeps under the scapula following the latissimus dorsi muscle, tapering inside toward the front of the body, curving down under the armpit and back up under the breast and pectoral muscle. Fifth pod 162 can land as far forward as the sternum or as far back as forward of center of the armpit area. The upper torso embodiment 152 is always located no lower than the tenth intercostal space in the rear of the rib cage and the sixth intercostal space in the front of the rib cage. It is also located no higher than the pectoral muscle in the front and the scapula in the rear of the body.

Figure 7A:
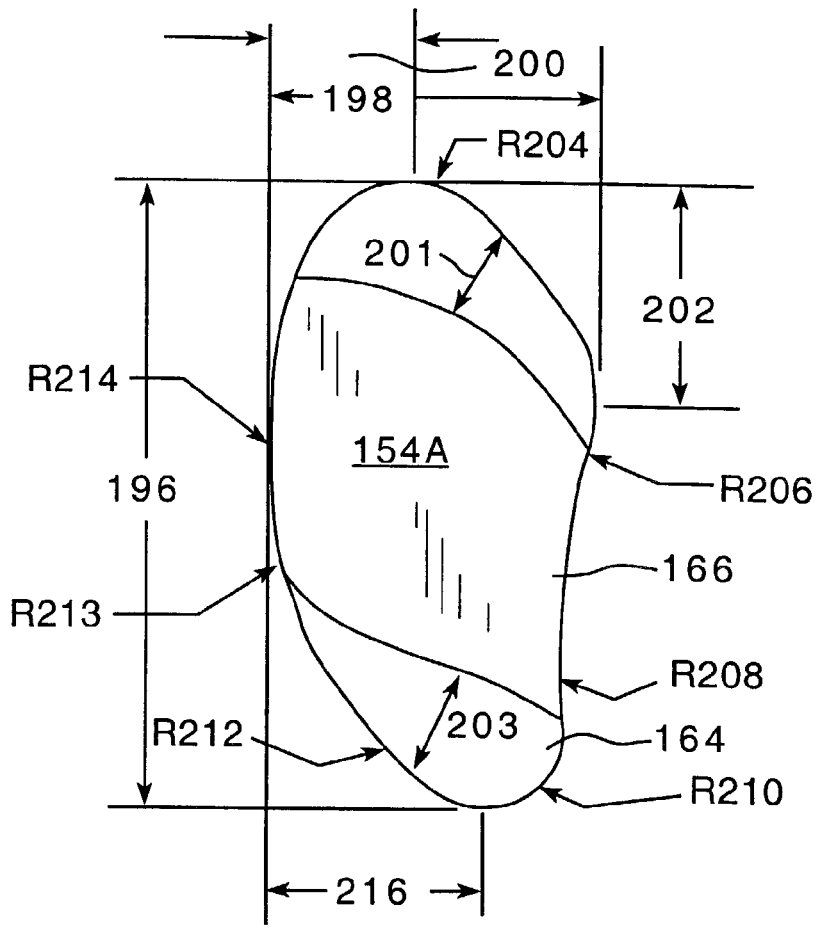
FIG. 7A is a plan view of a first pod mounted upon a rightmost half of an upper torso or rib cage pod set.
Figure 7B:
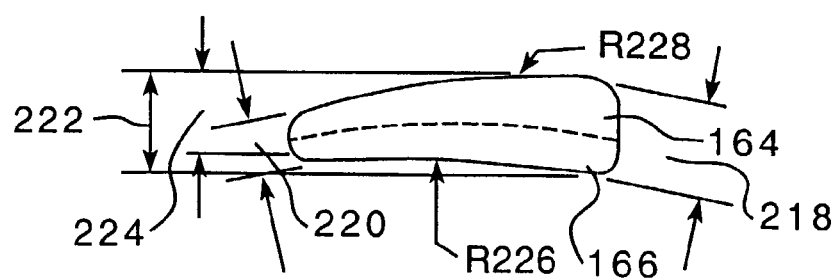
FIG. 7B is a side elevational view of the same first pod.

Referring now to FIG. 7, and with general references to FIG. 6, FIG. 7A shows pod 154A being the analogue of pod 154 for the rightmost section of the upper torso embodiment 152 having an overall height 196 of 5.01 inches and an overall width 198 of 2.66 inches. Pod 154A may generally be described as having three major areas, top and bottom convex sections 164 and a central concave section 166, forming a portion of the chamfer described earlier. The topmost convex section has a centerpoint length of 0.79 inches and the topmost curve R204 is provided with a radius of 0.88 inches. Radius R204 transitions leftwardly to radius 216 of 3.75 inches and rightwardly to concave radius R206 being 5.48 inches. A distance 202 of 1.74 inches is taken from the mid-point of the transitional curve between R206 and R204 to the topmost point of 154A. Radius R206 traverses downwardly and transitions to second concave radius R208 having a dimension of 3.68 inches, finally transitioning into bottommost radius R210 having a dimension of 0.63 inches. Radius R210 transitions leftwardly and upwardly into convex radius R212 having a dimension of 1.88 inches, which transitions at the point of intersection with the chamfer section 166 to radius R213 having a dimension of 3.75 inches. First upper torso pod 154A is also further defined by a dimensional width 200 from the mid-point of upper radius R204 to the leftmost edge of 1.13 inches and a lower partial width 216 from the mid-point of the bottommost curvature R210 to the leftmost edge having a value of 1.79 inches. Referring now to FIG. 7B, pod 154A is given a generally overall curved and tapered shape having its largest dimension at the rightwardmost edge 218 of 0.72 inches and its smallest dimension at the leftwardmost edge 220 of 0.42 inches. The relative sizing of the chamfered section 166 is shown in chain line. The pod has an overall thickness 222 of 0.76 inches and is provided with an inner radius R226 of 10 inches and an outer radius R228 of 5 inches, respectively.

Figure 7C:
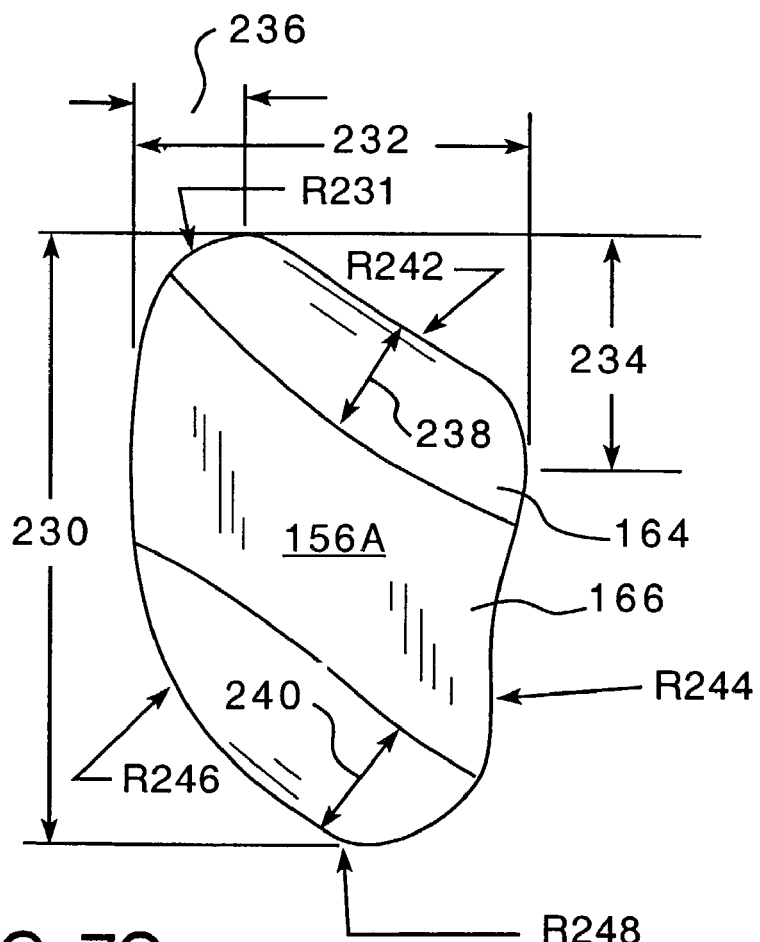
FIG. 7C is a plan view of a second pod of the same rightmost pod set.
Figure 7D:
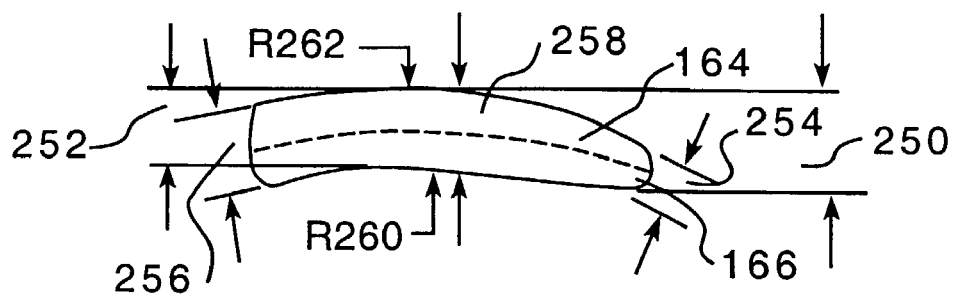
FIG. 7D is a side elevational view of the pod illustrated in FIG. 7C.

Referring now to FIG. 7C, second pod 156A has an overall height 230 of 5.48 inches and an overall width 232 of 3.04 inches. The distance 238 between chamfer 166 and the topmost section at the mid-point is 0.92 inches and has a general lower distance 240 of 1.0 inches. Starting at the topmost point, curve R231 is provided with a radius of 0.75 inches, which transitions in a rightward fashion into concave radius 242 of 8.59 inches. Concave radius R244, at the rightmost edge, is provided with a dimension of 4.38 inches which transitions at the lowermost point of the pod 156A to radius 248 having a dimension of 0.87 inches. Moving leftwardly, radius R248 transitions to radius R246, having a dimension of 10 inches, which joins radius R231 at the topmost point. Dimensionally pod 156A has a partial height 234 taken from the topmost point of pod 156A to the top rightmost corner transition of 1.67 inches in a dimension from the leftmost edge to the topmost point of radius R231 being a distance 236 of 0.84 inches. Referring to view D, chamfered section 166 is shown in chain line. The pod has an overall curved dimension and a taper from left to right edge having a maximum thickness 258 at the centerpoint of 0.60 inches and tapering leftwardly to a dimension 256 of 0.58 inches at the leftmost edge. Pod 156A is provided with an outermost radius surface R262 of 4.50 inches and an inner radius surface R260 having a dimension of 9.29 inches.

Figure 8E:
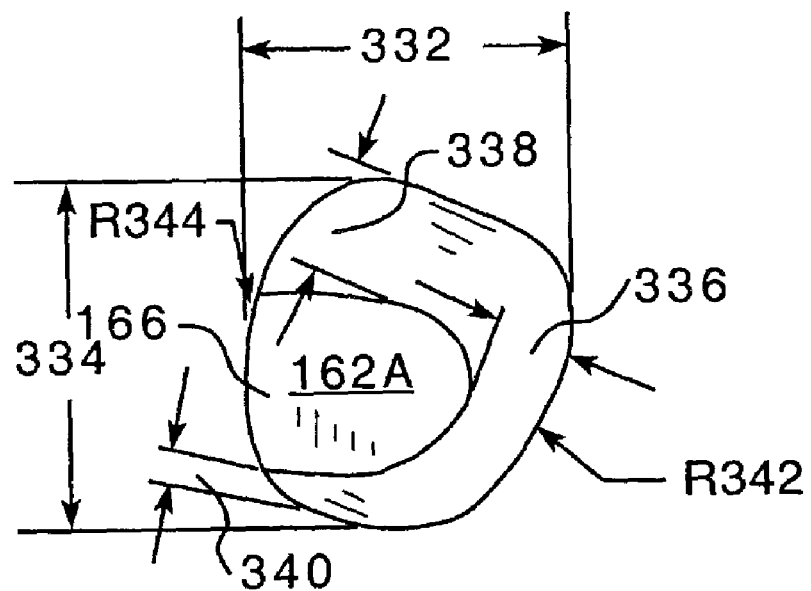
FIG. 8E is a plan view of a fifth pod of the same pod set.
Figure 8F:
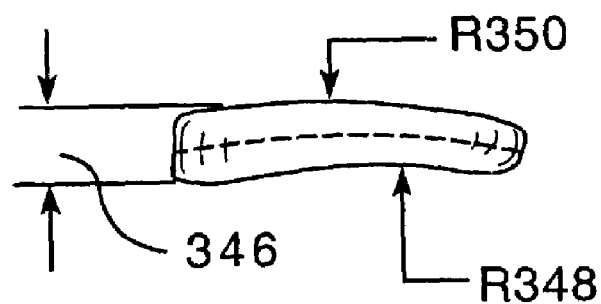
FIG. 8F is a side elevational view of the pod shown in FIG. 8E.

Referring now to FIG. 8, and generally to FIG. 6, FIG. 8A illustrates pod 158A having an overall width 264 of 3.36 inches and an overall height 266 of 3.70 inches. Pod 158A is provided with an uppermost distance 274 between chamfer 166 and the uppermost surface of 1.11 inches and a lowermost distance 276 of 0.55 inches measured at the mid-point of the distance between chamfer 166 and the lowermost edge of the pod 158A. At the uppermost edge of pod 158A, a concave radius R280 is provided having a radius of 8.59 inches. A partial width 270 measured from the leftmost terminal point of radius R280 to the leftmost edge of the pod 158A is 0.97 inches. Radius R280 transitions to rightmost radius R282 having a value of 5.93 inches. From the uppermost terminal point of radius R282, a distance 272 of 0.94 inches is measured to the topmost point of pod 158A. A partial height 268 of 1.24 inches of pod 158A is measured from the lowermost point of radius R282 to the lowermost point of pod 158A. Rightmost radius R282 transitions to radius R284 having a value of 1.13 inches to form the lower rightmost curve. Lower left curve is defined by radius R286 having a value of 1.12 inches transitioning into the leftmost concave radius R278 having a value of 4.38 inches. Referring to FIG. 8B, with chamfer 166 shown in chain line, the pod is generally curved and tapered from right to left having the major dimension at the rightmost edge 288 of 0.68 inches tapering to a minor dimension at the leftmost edge 290 of 0.37 inches. An outer face R298 is provided with a radius of 5 inches, and the inner face R294 is provided with a radius of 13.79 inches. Referring now to FIG. 8C, fourth pod 160A is provided with an overall width 302 of 2.67 inches and an overall height 300 of 2.78 inches. The distance between chamfer 166 and the uppermost surface 306 is 1.03 inches measured a distance 304 from the leftmost edge of pod 160A of 0.85 inches. The top edge of pod 160A is provided with concave radius R314 having a value of 8.59 inches. The rightmost edge of pod 160A is provided with radius R316 having a value of 2.33 inches which terminates a distance 312 from the bottom edge of pod 160A and having a value of 1.27 inches extending leftwardly from the rightmost point of pod 160A. A distance 310 of 2.04 inches begins radius R317 having a value of 0.62 inches which transitions from the lowermost edge to the leftmost edge having a convex radius R318 having a value of 5.93 inches. Referring now to FIG. 8D, with chamfered surface 166 shown in chain line, the pod is generally curved and tapered from left to right having a major dimension at the leftmost edge 324 of 0.59 inches tapering to a minor dimension 326 at the rightmost edge of 0.39 inches. At a mid-point, pod 160A has a depth 320 of 0.56 inches. Referring now to FIG. 8E, fifth pod 162A has an overall width 332 of 2.01 inches and an overall height 334 of 2.15 inches. Chamfered section 166 terminates at a distance 336 of 0.52 inches from the rightmost edge of pod 162A and is located a distance 338 of 0.78 inches from the topmost edge, and a distance 340 of 0.19 inches from the lowermost edge. Pod 162A has a major convex rightmost radius R342 of 1.56 inches, which transitions to flat top and bottom sections. The leftmost edge is provided with radius R344 having a value of 2.33 inches. Referring now to FIG. 8F, pod 162A has an overall thickness 346 of 0.46 inches and an outer surface radius R350 of 5 inches and an inner radius surface R348 of 8 inches.

Figure 9:
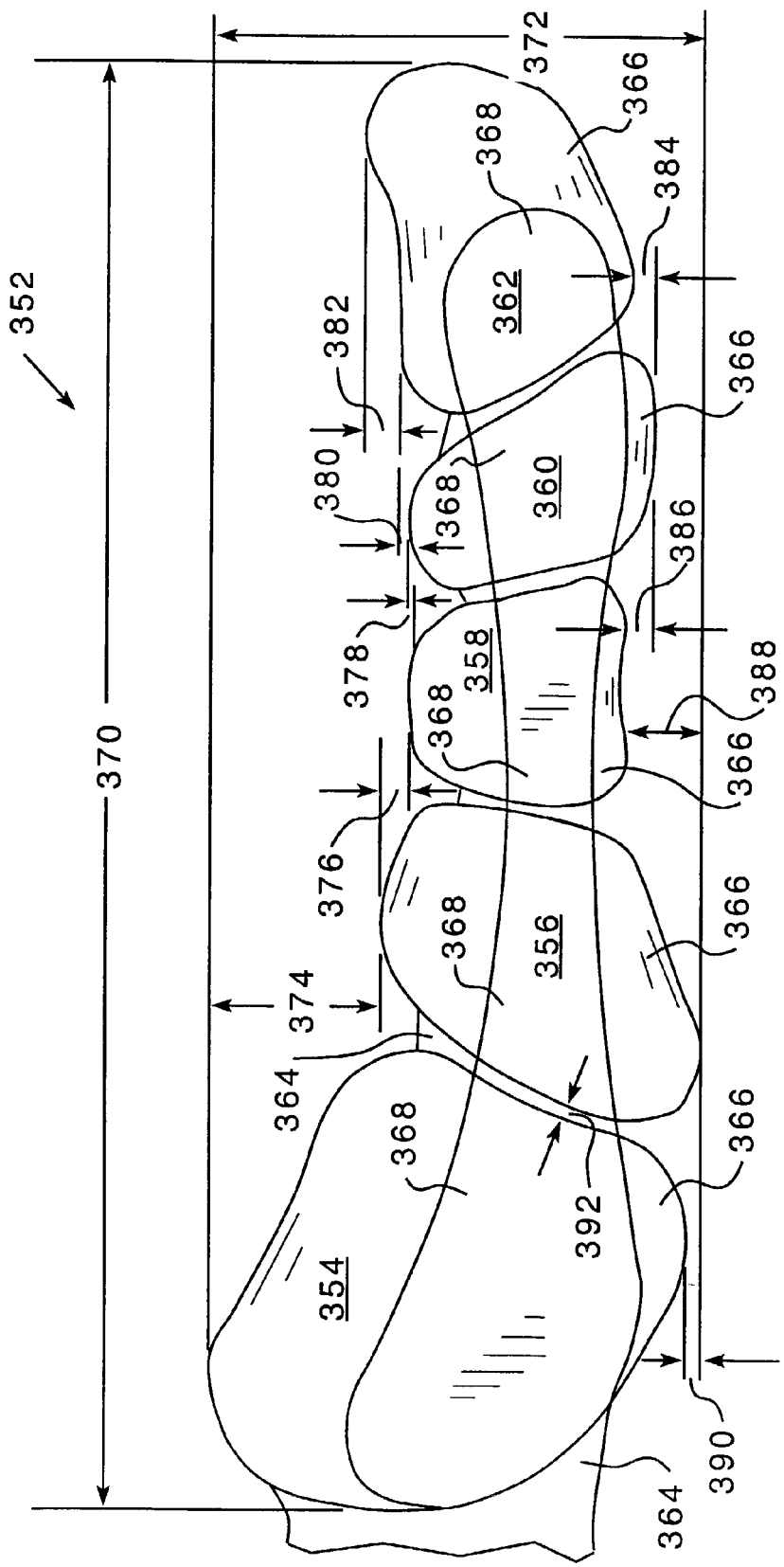
FIG. 9 is a plan view of the leftmost half of a lower torso-mounted pod set.

Referring now to FIG. 9, lower torso embodiment 352 is illustrated showing one-half of the entire apparatus, being the leftmost half, and be identical to the rightmost half as a mirror image. Lower torso embodiment 352 is comprised of five pods, 354, 356, 358, 360 and 362, on each side separated by approximately one-quarter to one inch of flexible material. The flexible material is centered on the spine just below the third lumbar vertebrae. Lower torso embodiment 352 is intended to follow the general curve of the iliac crest of the pelvis. The bottom profile of the set is defined by the line of the gluteus maximus and the hip joint. The pods continue around to the front of the body where they rest just under the flank pad. Fifth pod 362 can land as far forward as the lower abdomen muscles and as far back as to rest on the gluteus medias muscle. It is specifically intended that the flexible zones between the various pods of this embodiment are minimized. While the flexible section is preferably within the dimensions of the various pods, it may extend outwardly therefrom 3 to 5 inches upwardly or downwardly to cover the gluteus medias and the outer side of the gluteus maximus. Additionally, lower torso embodiment 352 can be joined in the front of the body through flexible areas having a width of approximately 3 to 4 inches connecting pods 362 and 362A. Lower torso embodiment 352 has an overall length of the five pods 370 of 14.41 inches. First pod 354 and second pod 356 comprise the maximum top and bottom dimensions having a total height 372 of 4.80 inches. Second pod 356 lies a distance 390 of 0.13 inches from its topmost point to the topmost point of adjacent pod 354, and lies a distance 374 of 1.63 inches from its lowest point to the lowest point of adjacent pod 354. Pod 358, at its lowest point, is disposed a distance 376 from the lowermost point of pod 356 being a distance of 0.25 inches. The lowermost point of fourth pod 360 lies a distance 378 from the lowermost point of third pod 358, being a distance of 0.06 inches. The lowermost point of fifth pod 362 lies a distance 382 from the lowermost point of fourth pod 360, being a distance of 0.36 inches. With respect to third, fourth and fifth pods 358, 360 and 362, respectively, pod 358 is displaced a distance 386 between its uppermost point and the uppermost point of pod 360, being a distance of 0.24 inches; while pod 362 at its uppermost point lies a distance 384 from the uppermost point of fourth pod 360, being a distance of 0.25 inches. Interpod distance 392 is typically uniform between the various pods, between 0.11 inches and 0.12 inches. The five pods are generally mounted upon a flexible member 364 and incorporate a chamfered area 368 roughly analogous to chamfered area 166 with reference to the upper torso embodiment 152.

Referring now to FIG. 10, with general reference to FIG. 9, illustration A depicts pod 354A, which is the mirror analogue to pod 354 shown in FIG. 9. Pod 354A is shown having a overall height 392 of 4.67 inches and an overall width 394 of 4.56 inches. An average distance 396 between the chamfer and the lowermost edge is 1.38 inches and the mid-point distance between the chamfer 368 and the topmost point of pod 354A 398 is 0.46 inches. The topmost point of pod 354A includes convex radius 404 having a value of 1.13 inches. This radius transitions rightwardly to radius R410 having a concave value of 4 inches, while the lowermost edge of pod 354A is formed from concave radius R395 having a value of 13.62. This transitions to radius R408 at the lowermost point of the pod 354A, having a value of 1.12 inches which finally transitions to the top leftmost edge radius R406 having a value of 3 inches. This transition occurs at a distance 400 between the topmost point and the R408 to R406 transition point having a value of 2.91 inches. Referring now to FIG. 10B, pod 354A has an overall thickness 420 of 1.05 inches, is generally curved and tapered toward the middle. Leftmost and rightmost maximum dimensions 422 and 424 are equal at 0.87 inches, and pod 354A has an outward surface radius R430 of 27.53 inches and an inner radius surface R428 of 21.64 inches. Radius R428 has a dimensional length 426 of 3.20 inches and is centered on the pod. Referring now to FIG. 10C, showing an elevation of pod 354A 90° displaced from that of FIG. 10B, the pod has an overall thickness 414 of 1.23 inches at its mid-point, tapering topwardly to a minimum dimension 412 of 0.85 inches and tapering at its lower end to a minor dimension 417 of 0.44 inches. Pod 354A has a inner convex curvature R416, having a value of 6 inches, and an outer convex curvature R418, having a value of 4 inches Referring now to FIG. 11, with general reference to FIG. 9, pod 356A is shown in illustration A having an overall height 432 of 2.67 inches and an overall width 434 of 3.79 inches. Chamfer 368 is disposed an average distance 438 from the bottom surface of pod 356A a distance of 1.12 inches and a distance 436 of 0.72 inches from the mid-point of top concave radius R440, itself having a dimension of 21.44 inches. Top radius R440 transitions rightwardly to radius R444 having a concave value of 10.62 inches, while R440 transitions leftwardly to convex radius R442 having a value of 4 inches. In section as shown in FIG. 11B, pod 356A has an overall thickness 446 of 1.04 inches, and is generally curved and slightly tapered, having a minimum dimension at the rightmost edge 448 of 0.73 inches and a maximum thickness at the leftmost edge 452 of 0.77 inches. Pod 356A in this section has an outward-facing curved surface R454 having a radius of 28.80, while the inner surface R456 has a radius of 28.80 inches. Referring to FIG. 11C, which is an elevation taken at a 90° angle from that shown in FIG. 11B, pod 356A has an outward radius R464 of 4 inches, an overall thickness 458 of 0.81 inches, and a topmost terminal thickness 460 of 0.64 inches tapering to a bottommost edge dimension 462 of 0.57 inches.

Referring now to FIG. 12, pod 358A is provided having a height 466 of 2.1 inches and a overall width 468 of 2.29 inches. Chamfer 368 is disposed a distance 472 from the topmost edge of pod 358A, being a distance of 0.22 inches, and a distance 470 from the lower edge of pod 358A, being a distance of 0.92 inches. The rightmost edge of pod 358A is provided with radius 474 having a value at 11.03 inches, while leftmost edge R476 is provided with a radius of 8.71 inches. Referring now to FIG. 12B, pod 358A is provided with an overall thickness 480 of 0.79 inches and has an interior surface radius R482 of 10 inches and an outer surface radius R484 of 5 inches. Referring to FIG. 12C, which shows an elevational view of pod 358A taken from a position 90° opposed from that of FIG. 12B, pod 358A is provided with an overall thickness 486 of 0.73 inches and an outer surface radius R488 of 4 inches.

Referring now to FIG. 13, with general reference to FIG. 9, pod 368 is shown in FIG. 13A as having an overall height 490 of 2.93 inches and an overall width 492 of 1.79 inches. Chamfer 368 is shown a distance 496 from the lowermost point of pod 360A having a dimension of 0.75 inches, and a distance 494 from the topmost surface having a value of 0.25 inches. The topmost surface R506 has a radius value of 6 inches, which transitions rightwardly to the right side edge R504 having a value of 8.85 inches. Lower edge R500 has a radius value of 13.62 inches, which transitions leftwardly to the arc section forming the lowermost point of pod 360A having a radius of 0.5 inches. Referring now to FIG. 13B, pod 360A is shown having an overall thickness 512 of 0.81 inches, an inner surface radius R516 having a value of 5 inches, and an outer surface radius R514 having a value of 2.87 inches. Referring now to FIG. 13C, which is an elevational view taken from a perspective 90° opposed from that of FIG. 13B, pod 360A has an overall thickness 518 of 0.99 inches and is generally curved and tapered from top to bottom, having a maximum thickness at the uppermost edge 520 of 0.81 inches and a minimum thickness at the lowermost edge 522 being 0.41 inches. Pod 360A is provided with an inner surface radius R528 of 5 inches and an outer surface radius R526 of 4 inches.

Figure 14A:
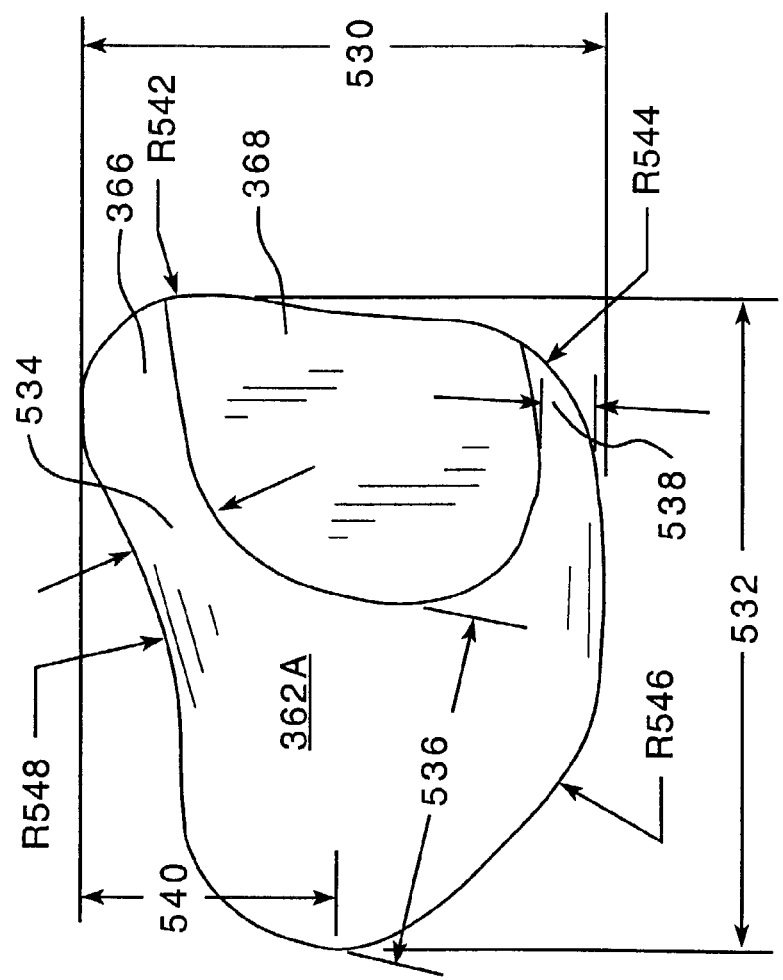
FIG. 14A is a plan view of a fifth pod of a leftmost half of a torso-mounted pod set.
Figure 14B:
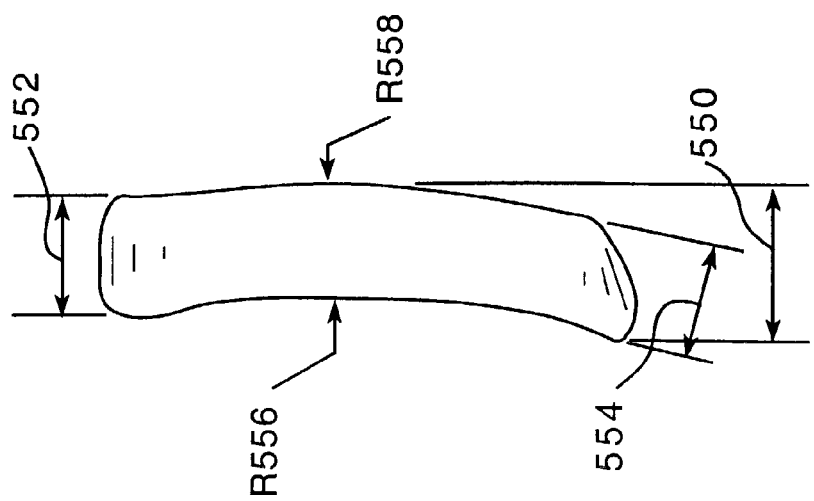
FIG. 14B is a first side elevational view of the pod illustrated in FIG. 14A.

Referring now to FIG. 14, with general reference to FIG. 9, end pod 362A is shown having an overall height 530 of 2.57 inches, and an overall width 532 of 3.33 inches. Chamfer 368 is disposed a distance 538 from the topmost edge of pod 362A being a distance of 0.225 inches, and a lower distance 534 from the lowermost edge of pod 362A a distance of 0.45 inches. Chamfer 368 terminates at a point interior to pod 362A being a distance 536 from the leftmost edge of pod 362A and having a value of 1.79 inches. Pod 362A is provided with an upper right radius 544 of 0.87 inches, which transitions leftwardly into radius 546 having a value of 4 inches. Lower surface 548 has a concave radius value of 4.41 inches. Referring now to FIG. B, pod 362A has an overall thickness 550 of 0.71 inches, and generally tapers from bottom to top having a maximum dimension at bottom edge 552 having a value of 0.55 inches, tapering to top edge 554 having a value of 0.53 inches.

Figure 15A:
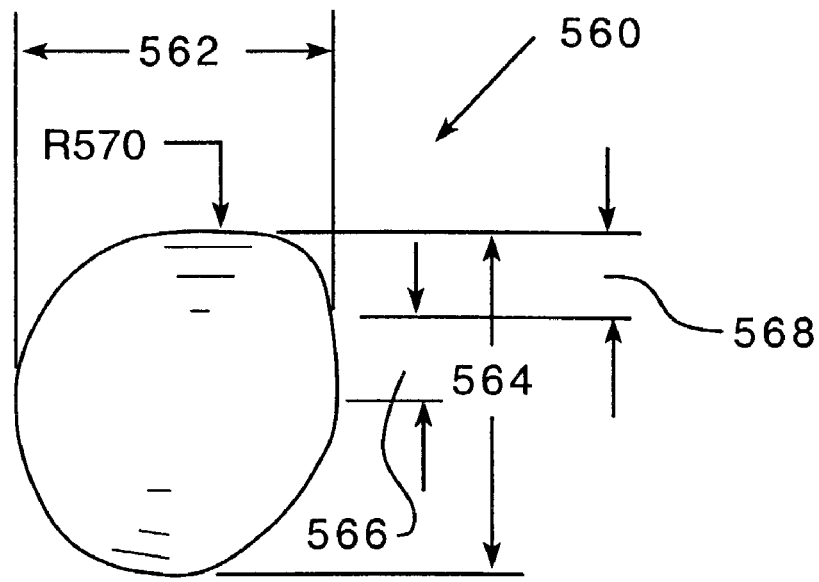
FIG. 15A is a plan view of the pod set of a forearm-mounted sensor apparatus.
Figure 15B:
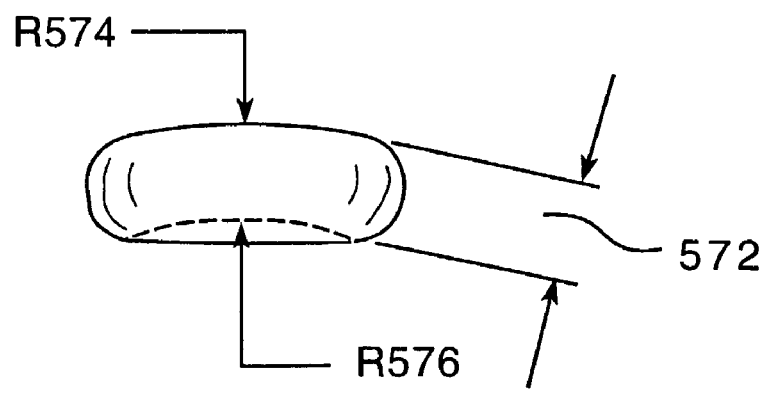
FIG. 15B is a side elevational view of the pod shown in FIG. 15A.

Referring now to FIG. 15, a forearm embodiment 560 is shown. Not illustrated but well understood to those skilled in the art, is a flexible cuff which envelops the wrist area having a typical length dimension of 4 inches into which the pod 560 is mounted. The pod for the forearm sits aside of the head of the ulna behind the wrist joint and on top of the tendons. The straightest edge of this roughly circular form follows the line from the tendon extending back from the forefinger. The flexible cuff that surrounds pod 560 encircles the arm and may be curved to avoid interference with the head of the ulna. The cuff could also extend the length of the forearm, curving under the bicipital fascia and wrapping upwardly along the line defined by the brachialis muscle. The small size and low profile of pod 560 are specifically intended to allow complex skeletal twisting and to permit the forearm to interact with the environment to enter various spaces on or around the body. Pod 560 is generally circular, having an angular protrusion extending roughly at right angles thereto defined by radius R570 having a value of 0.5 inches. Pod 560 generally has an overall width 562 of 1.38 inches and an overall height 564 of 1.52 inches. Flattened sections 566 generally have a length of 0.38 inches and are disposed a distance 568 which is 0.38 inches from the opposing surface. Referring now to FIG. 15B, pod 560 is generally curved, having overall thickness 572 of 0.44 inches and an inner surface radius R576 of 2.06 inches. Pod 560 is provided with an outer surface radius R574 of 2.5 inches.

Figure 16:
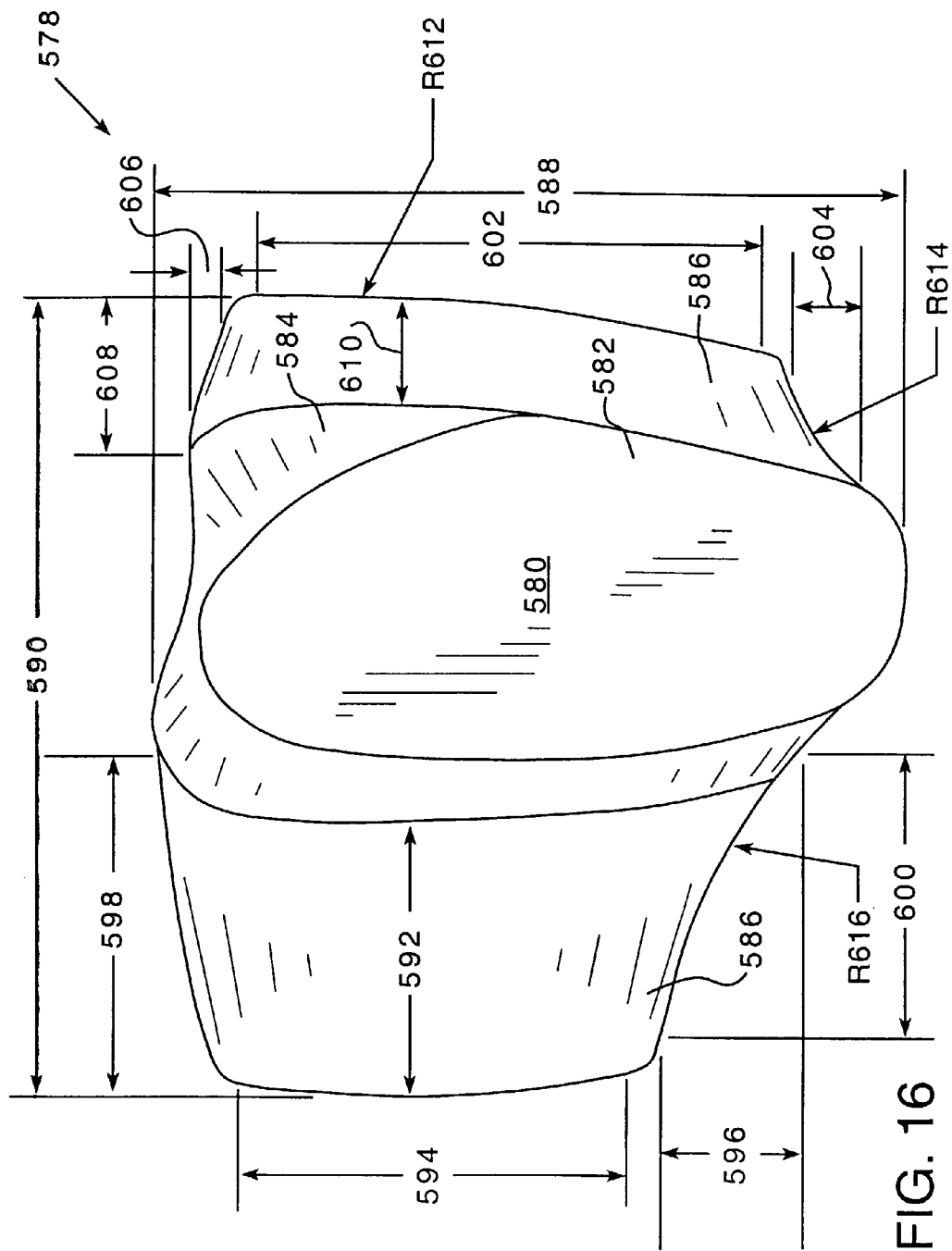
FIG. 16 is a plan view of a thigh-mounted embodiment of a pod.

Referring now to FIG. 16, thigh embodiment 578 is illustrated which is applied to the outer front of the leg, sits directly upon the outer upper portion of the quadriceps muscle of the thigh. The bottom profile of the form is designed to follow the line defined by the quadriceps tendon thereby keeping the pod on the muscle. The upper profile follows a concave curve. The flexible sections 586 wrap up to one-third of the distance around the thigh, extending one inch toward the front of the leg and three inches around the side of the leg. This placement keeps the pod out of the way for both walking and sitting. Curves in the profiles of the five pods are designed to allow the movement of the thigh muscles and the excess skin associated with the knee joint. The thigh pod is best attached to the body with straps that encircle the leg or as embedded in fitted pants. Thigh embodiment 578 is generally comprised of a rigid pod 580 mounted in conjunction with flexible section 586. Rigid pod 580 is further comprised of a generally convex top surface 582 and a chamfered section 584 extending around a portion of the perimeter. Thigh embodiment 578 has an overall width 590 of 7.52 inches and overall height 588 of 6.99 inches. The rightmost flexible section has a width 608, as measured at the topmost edge surface, of 1.5 inches. The rightmost edge of the flexible section is generally comprised of radius R612 having a length of 4.75 inches. At the bottommost portion, radius R612 transitions to convex radius R614 having an overall height 604 of 0.68 inches. The leftmost flexible section has an overall width, as measured from the top edge 598, of 3.16 inches, and a height of the major leftmost arcuate section 594 of 3.68 inches. A concave lower radius R616 is defined by a radius 5.49 inches and has an overall width 600 of 2.68 inches and a height 596 of 1.28 inches.

Figure 17A:
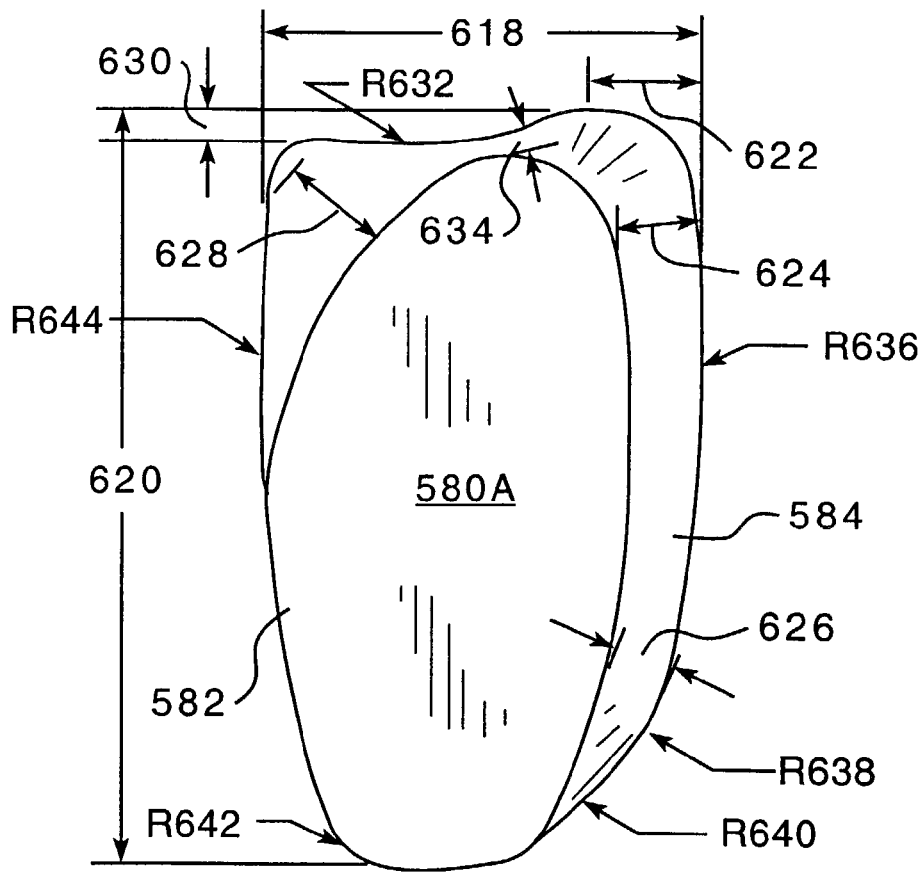
FIG. 17A is a plan view of the rigid pod section of the embodiment illustrated in FIG. 16.
Figure 17B:
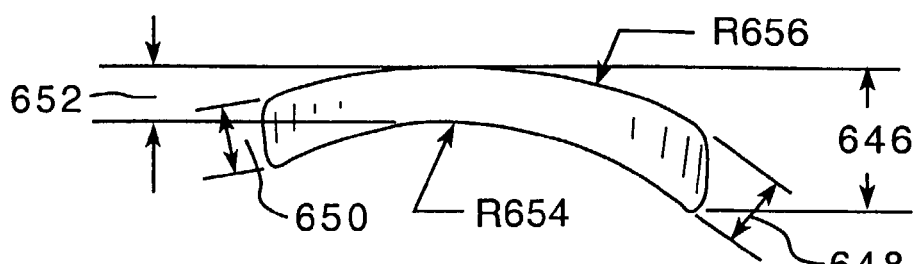
FIG. 17B is a side elevational view of the pod illustrated in FIG. 17A.

Referring now to FIG. 17, rigid pod 580A is provided with an overall height 620 of 6.96 inches and an overall width 618 of 3.95 inches. Chamfered section 584 extends for a distance 628 of 0.95 inches, excluding the radius corner, and narrows to a distance 634 of 0.21 inches at its narrowest point at the uppermost segment of the convex top surface 582. The chamfered surface has general width 624 along the rightmost edge of 0.73 inches, narrowing in a gradual taper moving toward the bottom surface of 0.54 inches at reference symbol 626, the upper termination point of the lower tapered section of chamfer 584. Pod 580A has a topmost edge surface having radius R632 of 4 inches and a rightmost convex radius R636 of 6.85 inches. R636 transitions, moving downwardly, to R638 at the tapered section having a radius of 1.50 inches at the transition, and a radius R640 of 5.49 inches at the termination point of the chamfer. The lower left corner of pod 580A is comprised of radius R642 having a value of 0.75 inches transitioning upwardly to radius R644 having a radius of 15 inches. Referring now to FIG. 17B, pod 580A has an overall thickness 646 of 1.26 inches and is generally curved and tapered in dimension having its maximum thickness at rightmost terminal edge section 648, having a value of 0.67 inches, transitioning to the minimum thickness at the leftmost edge 650, having a value of 0.61 inches. Outermost surface R656 has a radius of 5 inches, while interior surface has a concave radius R654 of 3.25 inches.

Figure 18:
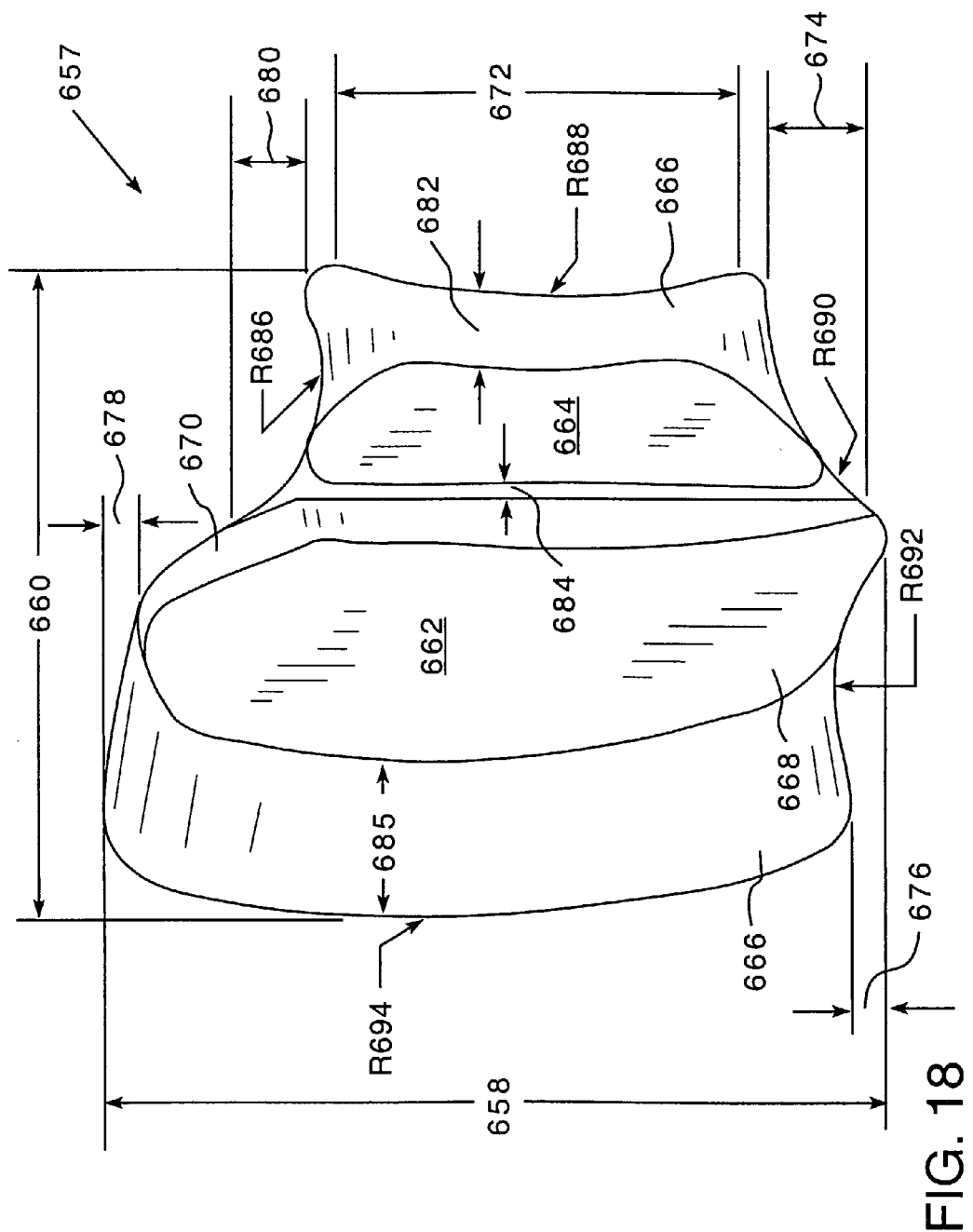
FIG. 18 is a plan view of a shin-mounted embodiment of a pod set.

Referring now to FIG. 18, the major and minor pods on the shin embodiment are connected by a flexible area which is typically one-quarter of an inch. The flexible area is centered on the furthest forward point or peak of the tibia shaft with the larger or major pod resting on the tibialis muscle, and the smaller pod or minor pod resting on the shaft of the tibia towards the inside of the shin. The sharp angle downward on the top profile of the shin pods follows the angle downward of the tibialis muscle. The outer edge of the major pod also follows a line defined by this muscle. The central location of the major pod on this tibialis muscle is critical to the placement of the form of the pod. The smaller or minor pod's outside profile is further defined by the inside soleus muscle. The flexible areas for the shin extend just to the edges of the tibialis and soleus muscles but could extend optionally to the complete circumference of the calf, curving underneath the large calf muscle, or gastrocnemius, and above the Achilles tendon. Shin embodiment 657 has an overall width 660 of 5.76 inches and an overall height 658 of 6.8 inches. Shin embodiment 657 is generally comprised of the major rigid pod 662 and minor rigid pod 664 mounted within a flexible section 666. Flexible section 666 extends leftwardly from major pod 662 a distance 685 being 1.42 inches, and has a leftmost edge R694 having a radius of 10.42 inches. The lower section of flexible member 666 adjacent major pod 662 has a concave radial edge R692 having a radius of 1.5 inches. A distance 676 of 0.27 inches separates the lower point of leftmost flexible section 666 with the lowest point of major pod 662, while the uppermost point of the flexible section extends a distance 678 being 0.29 inches above the uppermost point of major pod 662. Major pod 662 and minor pod 664 are separated by distance 684 being 0.11 inches. Flexible member 666 transitions rightwardly from major pod 662 through a concave radial section R686 having a radius of 1.6 inches, and extends a distance 682 rightward of major pod 664 being a distance of 0.64 inches. Rightmost edge section R688 of the flexible section is comprised of an arcuate surface R688 having a radius of 7.79 inches, and again transitions leftwardly back to the lowest point of major pod 662 through a radial section R690 having a radius of 2.06 inches and an overall height 674 of 0.88 inches.

Figure 19C:
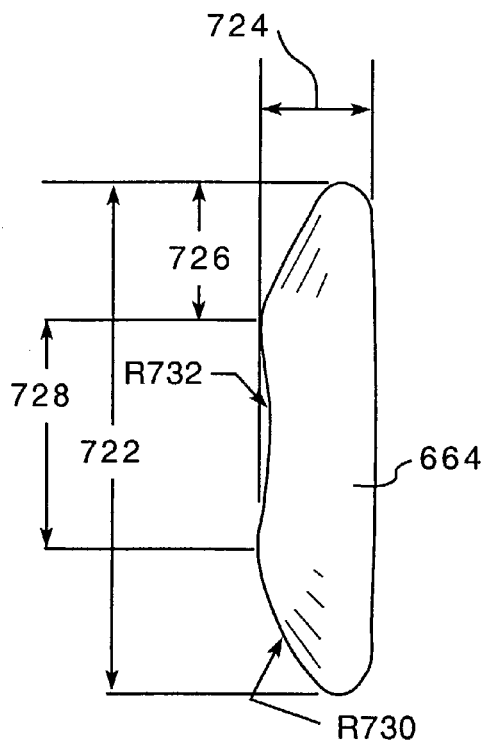
FIG. 19C is a plan view of a second pod illustrated in the pod set of FIG. 18.
Figure 19A:
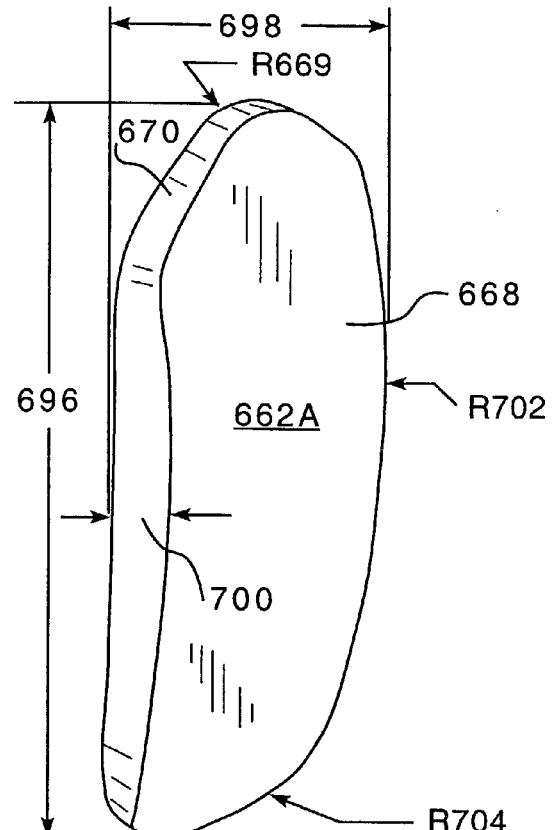
FIG. 19A is a plan view of a first pod mounted on the pod set illustrated in FIG. 18.
Figure 19D:
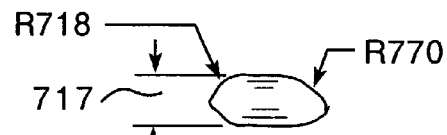
FIG. 19D is a side elevational view of the pod illustrated in FIG. 19C.
Figure 19B:
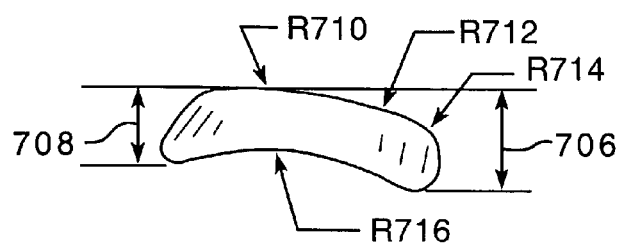
FIG. 19B is a side elevational view of the pod illustrated in FIG. 19A.

Referring now to FIG. 19A, major pod 662A has an overall height 696 of 6.5 inches and an overall width 698 of 2.42 inches. The rightmost surface is comprised of radial section R702 having a radius of 9 inches, which transitions downwardly to lower radial section R704 having a radius of 1.25 inches. The topmost point of pod 662A is comprised of a radial section R669 having a radius of 0.43 inches. A chamfered section 670 extends along the leftward side of pod 662A having an average width 700 of 0.51 inches. Referring now to FIG. 19B, pod 662A has an overall height 706 of 0.83 inches and is generally tapered down to a height 708 of 0.64 inches at the leftmost edge, excluding a sharp downward taper which includes the chamfer. The exterior top surface R710 incorporates a radial section at its centermost point having a radius of 3.96 inches transitioning to a radius at the rightmost corner R714 of 0.4 inches. Interior radial surface R716 has a radius of 2.25 inches. Referring now to FIG. 19C, minor pod 664 is shown having an overall height 722 of 4.51 inches and an overall width 724 of 1.05 inches. The leftmost edge is primarily comprised of a radius section R732 having a radius of 9.17 inches and extending a distance 728 of 2.03 inches located a distance 726 from the topmost edge being a distance of 1.22 inches. The lower third of the leftmost edge is comprised of a radius R730 having a radial distance of 1.65 inches. Referring to illustration D, pod 664 in section has an overall height 717 of 0.4 inches and a primary leftmost upper radial surface R718 of 0.25 inches tapering to rightmost radii R720 having a value of 0.38 inches.

Figure 20:
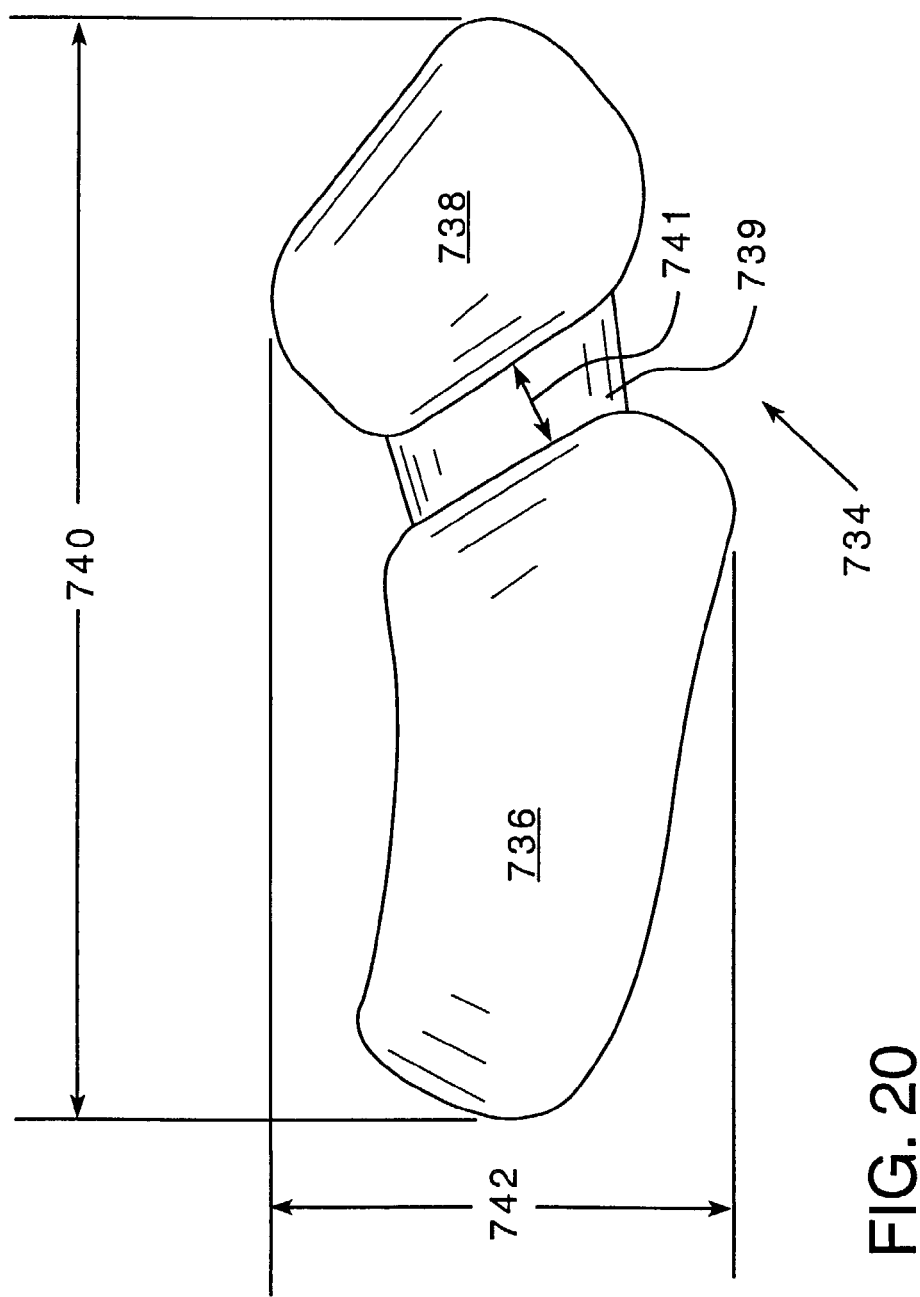
FIG. 20 is a plan view of a foot-mounted embodiment of a pod set.

Referring now to FIG. 20, foot embodiment 734 is primarily comprised of major pod 736 and minor pod 738 separated by a flexible section 739. The two pods of the foot embodiment rest on the top and outer side of the foot connected by a flexible area of approximately one-half inch width. The pods are at a slight angle to each other to accommodate a flexion over the complex curve of the top of the foot. The pod on the top of the foot has a straight vertical which follows the line of the tendon of big toe. The bottom profile curves back towards the heel following a line defined by the joints of each subsequent toe. The top profile of this pod is concave, and the flexible space between the two pods rests along the length of this last tendon of the small toe. The pod on the side of foot rests directly on the exterior digitorum brevis muscle following lines defined by the heel and ankle bones. The flexible areas of the foot embodiment could be extended to cover the entire top surface of the foot, curving around all the ankle and toe joints. Foot embodiment 734 has an overall length 740 of 7.28 inches and an overall height 742 of 3.04 inches. The pods are separated by a distance 741 of 0.60 inches.

Referring now to FIG. 21, FIG. 21A illustrates major pod 736A of foot embodiment 734 having an overall height 746 of 2.80 inches and an overall width 744 of 4.59 inches. The pod has a top radial section R756 having a radius of 6.33 inches and extending for a length 752 of 2.83 inches. The top section transitions rightwardly to radius section R762 having a radius of 0.5 inches, the mid-point of said radial section being a distance 750 from the lowermost point of pod 736A being a distance of 1.82 inches. The lower left radial section R758 has a radius of 0.75 inches and the leftmost section 748 extends for a lateral distance of 1.65 inches to the topmost edge. Referring to illustration B, pod 736A has an overall height 768 of 0.83 inches, is generally tapered from a thinner center section outwardly to each end. Rightmost edge 764 has a length of 0.58 inches and tapers to a minimum thickness of 0.36 inches at 766. Pod 736A tapers outwardly to leftmost edge 770 having a distance of 0.59 inches. Outer radial surface R778 has a radius of 10 inches while inner radial surface R776 has a value of 3.34 inches. Referring to illustration C, minor pod 738A has an overall width 788 of 1.99 inches and overall height 790 of 2.69 inches. This primarily comprised of a lower right radial section R792 having a radius of 1 inch, a lower left radial section R794 having a radius of 0.5 inches, and a left edge section R796 having a radial measurement of 22.17 inches. Referring now to the elevational view shown in illustration D, pod 738A has an overall thickness 782 of 0.55 inches and having a bottommost dimension 780 having a thickness of 0.48 inches which tapers outwardly to 0.82 inches and then inwardly again as the pod extends towards its topmost section 784 having a width of 0.26 inches. The outermost surface R786 has a radial value of 8 inches.

Figure 22:
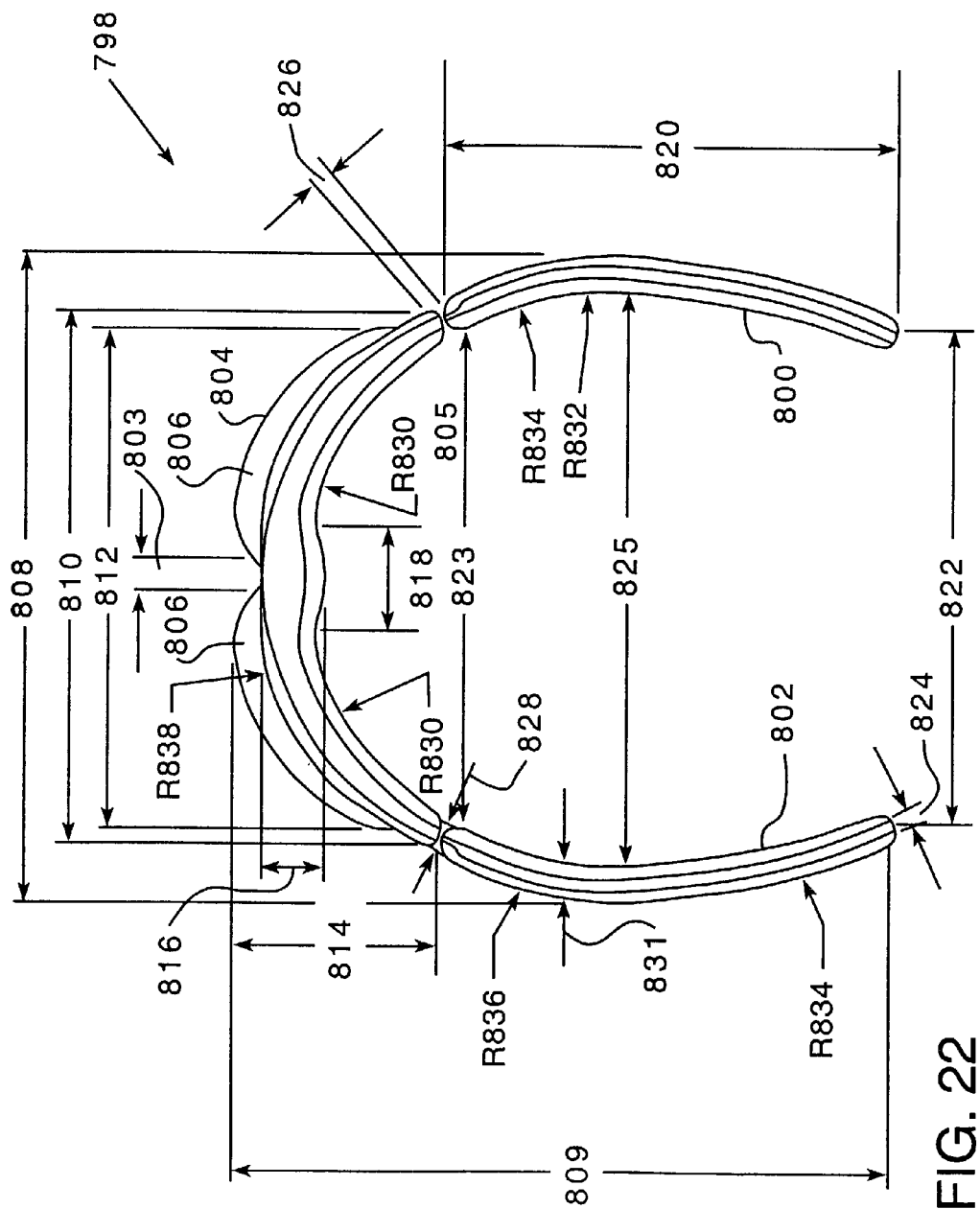
FIG. 22 is a plan view of a cranium-mounted embodiment of a pod set.

Referring now to FIG. 22, a head embodiment 798 is provided having three pod sections, a leftmost section 800, a rightmost section 802, and a top section 805.

Figure 23:
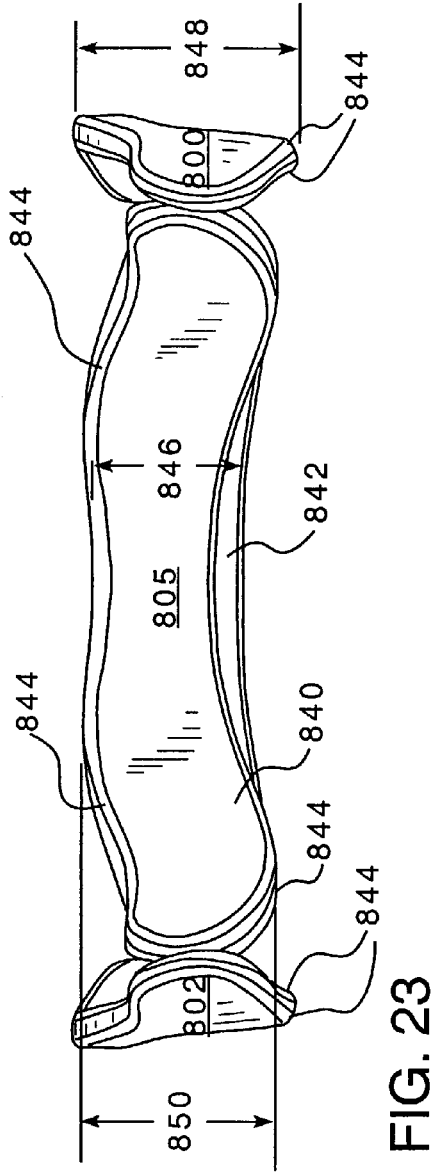
FIG. 23 is a front elevational view of the pod set illustrated in FIG. 22.
Figure 24:
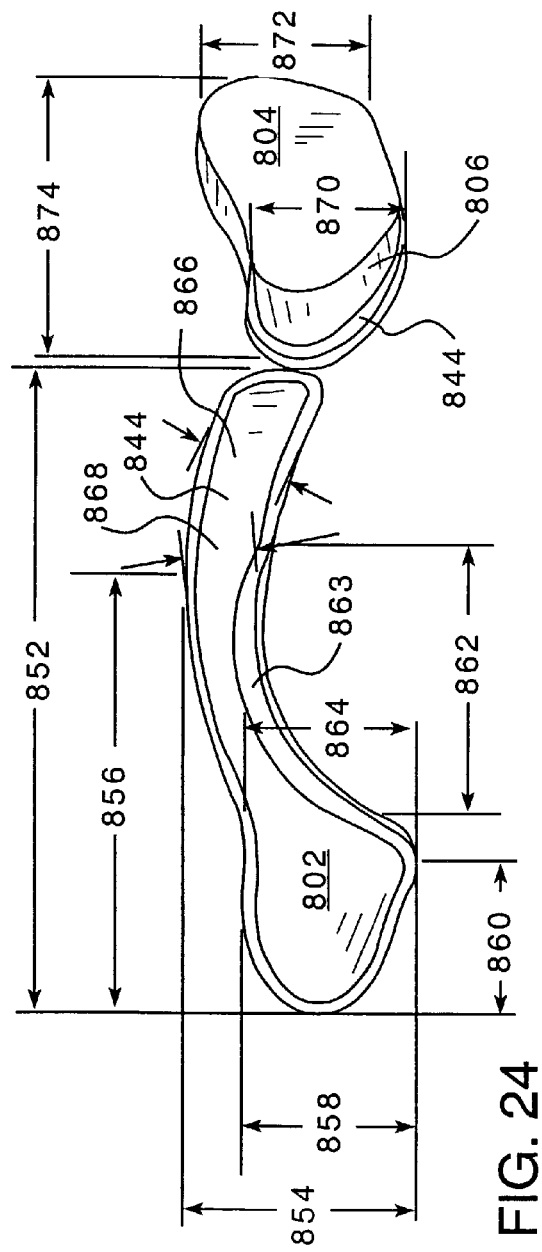
FIG. 24 is a side elevational view of a portion of the pod set illustrated in FIG. 22.

Referring now to FIGS. 22, 23 and 24, the head embodiment 798 is mounted behind the temples but above the cheekbone above the ear, resting on the temporalis muscle. Rear portion 805 centers itself under the external occipital protuberance and is affixed to left and right sections 800 and 802, respectively, through a flexible layer, which is not shown. An optional flexible section connecting the front ends of sections 802 and 800 is also contemplated. Rear section 805 is an overall length 810 of 5 inches and an overall depth 814 of 1.82 inches and an overall height 850 of 1.29 inches. The inner or front surface is comprised of three major sections, the primary radial section R831, on both left and right sides, of 3.09 inches; a transitional radial section R830 of 1.25 inches; and a center convex radial section 818 of 1.25 inches. The rearmost surface of rear section 805 contains rigid pods 806 having rearward facing surfaces 804. Pods 806 are mounted to arcuate sections R838, measuring 2.43 inches, and are separated by distance 803 of 0.33 inches. The pod section has a total width 812 of 4.68 inches while the entire headpiece has an overall width 808 of 6.04 inches. The rear section 805 is separated from right and left sections 800 and 802 by flexible section 826 having a distance of 0.14 inches. Rear section 805 has an overall height 872 of 1.04 inches, while the side sections have an overall length 820 of 4.08 inches and an overall height 848 of 1.43 inches. Each of the three segments is chamfered at the perimeter on both interior and exterior surfaces 844. Rear section 805 has an additional lower chamfer 842. Each of the side sections 802 and 800 have an overall length 852 of 4.13 inches, an interior chamfered segment 863 having an overall length 862 of 1.73 inches and are preferably constructed of 90D material. Each segment extends forwardly from rear section 805 with an initial height 866 of 0.54 inches tapering down to a height 868 of 0.45 inches. A temporal flange at the forwardmost portion of side pieces 800 and 802, has an overall height 864 of 1.06 inches tapering to a forward pointed section extending a distance 860 of 0.96 inches from the widest point of the temporal flange.

In operation, at least one sensor is mounted within the pod member. The precise location of the sensor is wholly dependent upon the nature of the human physiological status data which is to be collected. Certain sensors require direct contact with the skin, while others require only mounting in a location proximate to the body surface. The appropriate pod location is determined from physiological data which is well within the knowledge of those skilled in the art of human physiological data acquisition.

Figure 25:
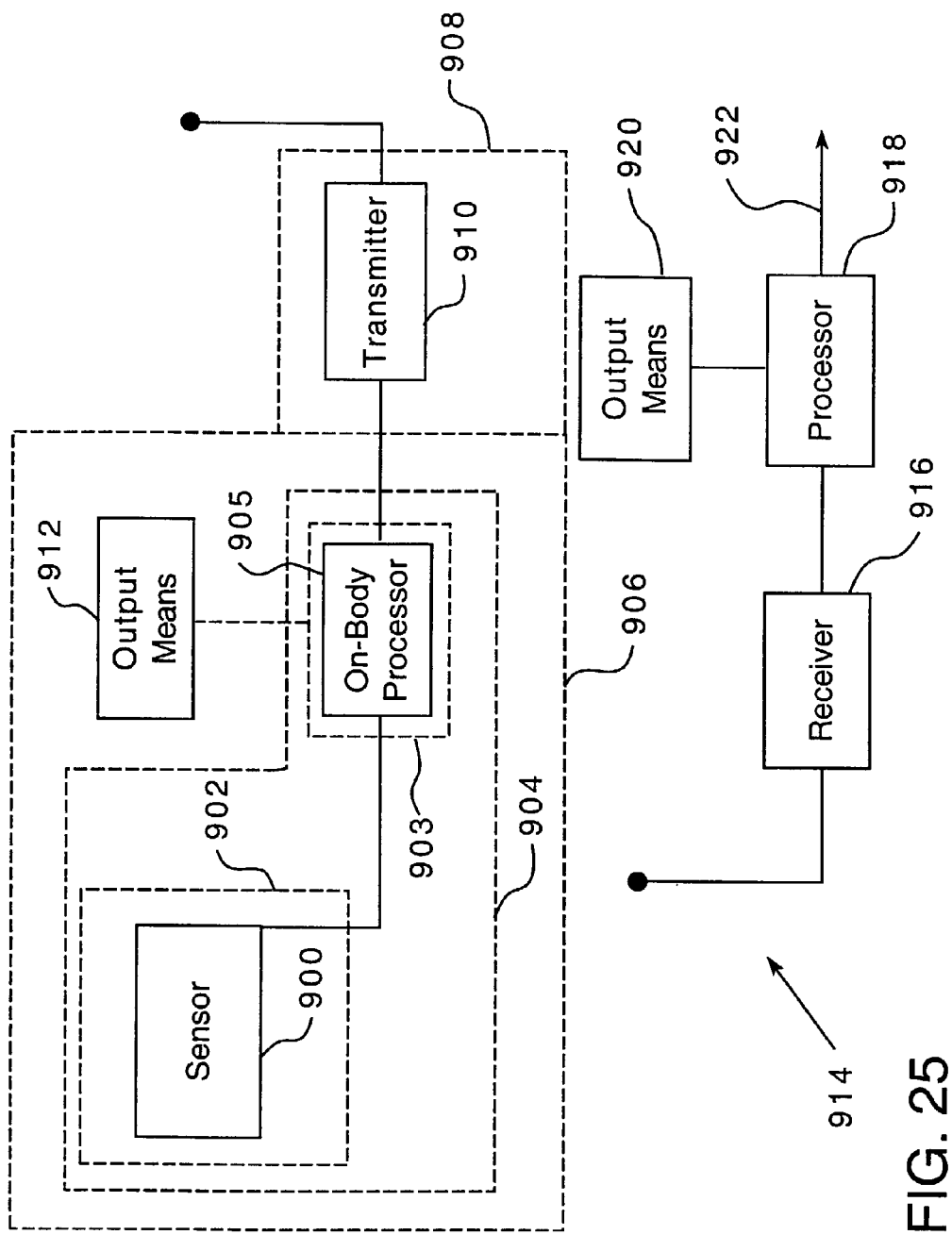
FIG. 25 is a block diagram of the electrical components of the system.

Referring now to FIG. 25, a sensor or sensor array 900 is mounted within a pod 902. Processing means 905, which may or may not be incorporated with data storage memory may be located in a separate pod 903 or within the same pod 904 as sensor array 900. The physical location of the sensors and electronic components is primarily a function of size and convenience. It is anticipated that with the current and future development of small, dedicated processors and miniaturized circuitry, that the processor means 905 will be mounted within the same pod 904 as the sensors 900. The rigidity of the pod 900 is intended to protect the sensors and circuitry from damage by physical contact as well as environmental conditions. The flexible sections which surround and interconnect the rigid pod sections are sized and intended to carry flexible electronic wiring and other data transmission means, such as optical fiber. Wireless technologies might also be utilized to connect even the basic sensor and processor apparatus. A transmitter 910 might be placed in a separate pod 908, or combined with any of the sensor or processor pod sections.

As applied to the human body, a sensor would be mounted within a pod and intended to detect a certain physiological or environmental status. The sensor would electronically emit an electrical signal which would be passed to the processor according to conventional methodology. The processor, if designed for onboard processing, would track the various data points detected by the sensor and store this data in memory, preferably in the form of a database. In this manner, all data from the various sensors mounted to the body could be correlated in terms of time and location. This data could then be interpreted by onboard software to detect certain changes or thresholds of physical activity or condition. This information could be stored for batch retrieval at certain times, or transmitted in a continuous, real-time stream of data. The processing means 905, in one embodiment, construct certain graphical, numerical or electronic output data which would be passed to the output means 912. Output means 912 is intended to range from a simple LED indicator light to a graphical display, which might be incorporated in a pod or worn as a watch, for example. Other methodologies of feedback to the user include auditory, tactile and haptic indicators or alarms, which would signal the passage of the sensor data through a preset threshold. It is specifically intended that more than one output means may be utilized simultaneously.

Transmitter 910 is adapted to take the output data from processor 905 and transmit the same to a monitoring facility 914. This may occur in the event that the user receives direct output or not. Certain embodiments may also utilize only rudimentary data acquisition and capturing facilities within the processor 905 and pass this raw data to transmitter 910 for processing within monitoring facility 914. In either event, monitoring facility 914 is comprised of a receiving means 916, a processing means 918 and an output means 920. These are assembled according to methodologies well known to those skilled in the art, and may be incorporated within the functionality of a personal computer. This would also enable the data to be further transmitted by computer transmission 922 to any external data storage or output source through telecommunication or other network data sharing modalities.

The terms and expressions which have been employed here are used as terms of description and not as limitation, and there is no intention in the use of such terms and expressions of excluding equivalents of the features shown and described or portion thereof, it being recognized that various modifications are possible within the scope of the invention claimed.

Although particular embodiments of the present invention have been illustrated in the accompanying drawings and described in the foregoing detailed description, it is to be further understood that the present invention is not to be limited to just the embodiments disclosed, but that they are capable of numerous rearrangements, modifications and substitutions.

What is claimed is:

1. An apparatus for detecting and reporting data relating to at least one of a human physiological and environmental condition, said apparatus adapted to be placed within at least one defined, preselected space proximate to a human body such that said apparatus avoids interference with the motion and flexibility of said human body, said apparatus comprising:

a rigid pod having an inner surface adapted to accept an exterior surface of said human body and a convex outer surface, said inner surface of said pod having a convex portion adapted to be received by a generally concave portion of said exterior surface of said human body, said inner surface further having an outer edge, at least a portion of said pod being radiused at said outer edge of said inner surface;

at least one sensor detecting at least one of a physiological conditional data point and an environmental conditional data point, said at least one sensor being mounted to said pod;

processing means in electrical communication with said at least one sensor for converting said at least one data point from said at least one sensor into at least one of human physiological and environmental status output data; and output means in electrical communication with said processing means for communicating said output data to a user.

2. An apparatus according to claim 1, further comprising a flexible section, said rigid pod being supported by said flexible section.

3. An apparatus according to claim 2, said at least one sensor being supported by said flexible section.

4. An apparatus according to claim 2, said at least one sensor comprising two or more sensors, a first one of said two or more sensors being supported by said flexible section and a second one of said two or more sensors being supported by said rigid pod.

5. An apparatus according to claim 1, further comprising wrapping means coupled to said flexible section for maintaining contact between said pod and said human body.

6. An apparatus according to claim 1, further comprising a wireless transmitting device for transmitting at least one of said at least one data point and said output data to a receiving and processing device.

7. An apparatus according to claim 6, wherein said processing means and said transmitting means are mounted in said pod.

8. An apparatus according to claim 1, said pod having a width dimension as measured between a first lateral side and a second lateral side of said pod, at least a portion of said first lateral side and said second lateral side each having a taper such that said width dimension gradually decreases in a direction from said inner surface to said outer surface.

* * * * *